(12) United States Patent
Ly et al.

(10) Patent No.: US 8,314,116 B2
(45) Date of Patent: Nov. 20, 2012

(54) 2-S-BENZYL SUBSTITUTED PYRIMIDINES AS CRTH2 ANTAGONISTS

(75) Inventors: Tai Wei Ly, San Diego, CA (US); Garrett Thomas Potter, Redlands, CA (US); Marie Chantal Siu-Ying Tran, Arcadia, CA (US)

(73) Assignee: Actimis Pharmaceuticals, Inc., San Diego, CA (US)

(*) Notice: Subject to any disclaimer, the term of this patent is extended or adjusted under 35 U.S.C. 154(b) by 247 days.

(21) Appl. No.: 12/679,893

(22) PCT Filed: Sep. 24, 2008

(86) PCT No.: PCT/US2008/011054
§ 371 (c)(1), (2), (4) Date: Jun. 7, 2010

(87) PCT Pub. No.: WO2009/042139
PCT Pub. Date: Apr. 2, 2009

(65) Prior Publication Data
US 2010/0240685 A1    Sep. 23, 2010

Related U.S. Application Data

(60) Provisional application No. 60/995,387, filed on Sep. 25, 2007.

(51) Int. Cl.
C07D 239/47 (2006.01)
A61K 31/505 (2006.01)
(52) U.S. Cl. .................................... 514/274; 544/317
(58) Field of Classification Search ............... 544/317; 514/274
See application file for complete search history.

(56) References Cited

U.S. PATENT DOCUMENTS

| | | | |
|---|---|---|---|
| 7,750,014 B2 | 7/2010 | Ly et al. | |
| 7,812,160 B2 | 10/2010 | Ly et al. | |

FOREIGN PATENT DOCUMENTS

| | | |
|---|---|---|
| DE | 42 39 440 | 6/1993 |
| EP | 1 170 594 | 1/2002 |
| EP | 1 413 306 | 4/2004 |
| EP | 1 471 057 | 10/2004 |
| GB | 1356834 | 6/1974 |
| GB | 2262096 | 3/1992 |
| WO | WO 01/58902 | 8/2001 |
| WO | WO 01/83485 | 11/2001 |
| WO | WO 2004/058164 | 7/2004 |
| WO | WO 2005/073234 | 11/2005 |
| WO | WO 2009/042138 | 4/2009 |

OTHER PUBLICATIONS

Ulrich, Chapter 4:Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
West, Solid Solutions, Solid State Chemistry and its applications, pp. 358 & 365, 1988.*
Kostenis et al., Emerging roles of DP and CRTH2 in allergic inflammation, TRENDS in Molecular Medicine, vol. 12, No. 4, pp. 148-158, Apr. 2006.*
Hata et al., Pharmacology and Signaling of prostaglandin receptors: Multiple roles in inflammation and immune modulation, Pharmacology & Therapeutics, 103, pp. 147-166 (2004).*
Pettipher, The roles of the prostaglandin D2 receptors DP1 and CRTH2 in promoting allergic responses, British Journal of Pharmacology, 153, pp. S191-S199 (2008).*
Robinson, Medical Therapy of Inflammatory Bowel Disease for the 21$^{st}$ Century, Eur J Surg, Suppl 582, pp. 90-98 (1998).*
Singh et al., Immune therapy in inflammatory bowel disease and models of colitis, British Journal of Surgery, 88, 1558-1569 (2001).*
Ordukhanyan, A. A., et al, Khimiko-Farmatsevticheskii Zhurnal, 13(9): 36-40 (1979) (English abstract provided).
Ly, T. W., et al, Small-Molecule CRTH2 Antagonists for the Treatment of Allergic Inflammation: An Overview, Expert Opin. Investig. Drugs, 14(7): 769-773 (2005).
Sugimoto, H., et al, An Orally Bioavailable Small Molecule Antagonist of CRTH2, Ramatroban (Bay U3405), Inhibits Prostaglandin D2-Induced Eosinophil Migration in Vitro, J. Pharmacology & Experimental Therapeutics, Am. Soc. for Pharmacology and, U.S., vol. 305, No. 1, pp. 347-352 (2003).
Ulven, T., et al, Novel Selective Orally Active CRTH2 Antagonists for Allergic Inflammation Developed from in Silico Derived Hits, J. Med. Chem., 49, pp. 6638-6641 (2006).
Yamamoto et al., "The orally available spleen tyrosine kinase inhibitor 2-[7-(3,4-dimethoxyphenyl)-imidazo [1,2-c] pyrimidin-5-ylamino]-nicotinamide dihydrochloride (BAY 61-3606) blocks antigen-induced airway inflammation in rodents," J Pharmacol Exp Therapeutics 306(3):1174-1181 (2003).
Office Action in U.S. Appl. No. 10/554,668 mailed Dec. 9, 2009.
Notice of Allowance in U.S. Appl. No. 10/554,668 mailed May 25, 2010.
Office Action in U.S. Appl. No. 10/585,429 mailed Oct. 1, 2009.
Notice of Allowance in U.S. Appl. No. 10/585,429 mailed Apr. 5, 2010.

* cited by examiner

Primary Examiner — Deepak Rao
(74) Attorney, Agent, or Firm — Jones Day

(57) ABSTRACT

Provided herein are 2-S-benzyl pyrimidine compounds having CRTH2 (G-protein-coupled chemoattractant receptor, expressed on Th2 cells) antagonistic activity, useful for the prophylaxis and treatment of diseases associated with CRTH2 activity, including the treatment of allergic diseases, eosinophil-related diseases and basophil-related diseases.

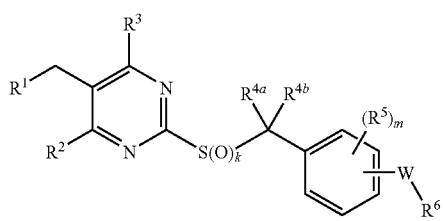

37 Claims, No Drawings

2-S-BENZYL SUBSTITUTED PYRIMIDINES AS CRTH2 ANTAGONISTS

CLAIM OF PRIORITY

This application is a 371 of International Patent Application No. PCT/US2008/011054, filed on Sep. 24, 2008, which claims priority to U.S. Provisional Patent Application No. 60/995,387, entitled "2-S-benzyl substituted pyrimidines as CRTH2 antagonists," filed Sep. 25, 2007. The disclosure of each of the above-referenced applications is incorporated by reference herein in its entirety.

FIELD OF THE INVENTION

Provided herein are 2-S-benzyl pyrimidine compounds having CRTH2 (G-protein-coupled chemoattractant receptor, expressed on Th2 cells) antagonistic activity, useful for the prophylaxis and treatment of diseases associated with CRTH2 activity, including the treatment of allergic diseases, eosinophil-related diseases and basophil-related diseases.

BACKGROUND

CRTH2 is a G protein-coupled chemoattractant receptor, expressed on Th2 cells, eosinophils, and basophils (Nagata et al., *J. Immunol.*, 162:1278-1286, 1999; Hirai et al., *J. Exp. Med.*, 193: 255-261, 2001).

Th2 polarization has been observed in allergic diseases such as asthma, allergic rhinitis, atopic dermatitis and allergic conjunctivitis (Romagnani, S., *Immunology Today*, 18: 263-266, 1997; Hammad et al., *Blood*, 98: 1135-1141, 2001). Th2 cells regulate allergic diseases by producing Th2 cytokines such as IL-4, IL-5 and IL-13 (Oriss et al., *J. Immunol.*, 162: 1999-2007, 1999; Viola et al., *Blood*, 91:2223-2230, 1998; Webb et al., *J. Immunol.*, 165: 108-113, 2000; Dumont, F. J., *Exp. Opin. Ther. Pat.*, 12: 341-367, 2002). These Th2 cytokines directly or indirectly induce migration, activiation, priming and prolonged survival of effector cells, such as eosinophils and basophils, in allegic diseases (Sanz et al., *J. Immunol.*, 160: 5637-5645, 1998; Pope et al., *J. Allergy Clin. Immunol.*, 108: 594-601, 2001; Teran, L. M., *Clin. Exp. Allergy*, 29: 287-290, 1999).

Prostaglandin $D_2$ ($PGD_2$), a ligand for CRTH2, is produced from mast cells and other important effector cells in allergic diseases (Nagata et al., *FEBS Lett.*, 459: 195-199, 1999; Hirai et al., *J. Exp. Med.*, 193: 255-261, 2001). The activation of CRTH2 by $PGD_2$ induces the migration and activation of Th2 Cells and eosinophils, suggesting that CRTH2 may play a pro-inflammatory role in allergic diseases (Hirai et al., *J. Exp. Med.*, 193: 255-261, 2001; Gervais et al., *J. Allergy Clin. Immunol.*, 108: 982-988, 2001). Therefore, antagonists which inhibit the binding of CRTH2 and $PGD_2$ should be useful for the treatment of allergic diseases, such as, asthma, exercise induced asthma, allergic rhinitis, atopic dermatitis and allergic conjuncitivitis.

In addition, experimental evidence has demonstrated the contribution of eosinophils in sinusitis (Hamilos et al., *Am. J. Respir. Cell and Mol. Biol.*, 15: 443-450, 1996; Fan et al., *J. Allergy Clin. Immunol.*, 106: 551-558, 2000), and Churg-Strauss syndrome (Coffin et al., *J. Allergy Clin. Immunol.*, 101: 116-123, 1998). In the tissues of these patients, mast cells can be observed to be colocalized with eosinophils (Khan et al., *J. Allergy Clin. Immunol.*, 106: 1096: 1101, 2000). It is suggested that $PGD_2$ production from mast cells induces the recruitment of eosinophils. Therefore, CRTH2 antagonists are also useful for the treatment of other eosinophil-related diseases such as Churg-Strauss syndrome and sinusitis. CRTH2 antagonists can be useful for the treatment of some basophil-related diseases such as basophilic leukemia, chronic urticaria and basophilic leukocytosis, because of the high expression of CRTH2 on basophils.

Thus, there is a need for the development of compounds with CRTH2 antagonistic activity for the treatment of CRTH2-mediated disorders or diseases.

SUMMARY OF THE INVENTION

Provided herein are 2-S-benzyl pyrimidine compounds that are CRTH2 antagonists, pharmaceutical compositions containing the compounds and methods of use thereof. In certain embodiments, the compounds for use in the compositions and methods provided herein are of the formula:

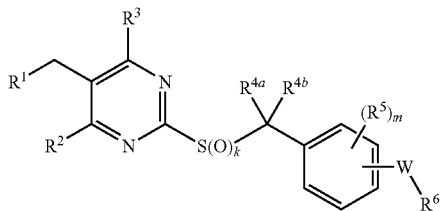

or a pharmaceutically acceptable salt, solvate, hydrate, stereoisomer or tautomer thereof, wherein the variables are chosen such that the resulting compound shows activity as a CRTH2 antagonist.

Pharmaceutical compositions containing a compound of the formula above and a pharmaceutically acceptable carrier or excipient are provided herein. Also provided are methods for treating CRTH2 mediated diseases or symptoms thereof by administering the compounds and compositions provided herein.

In certain embodiments, provided herein are methods for modulating an action of CRTH2 receptor by contacting the receptor with a compound or composition provided herein. In one embodiment, provided herein are methods for antagonizing an action of CRTH2 receptor by contacting the receptor with a compound or composition provided herein. In another embodiment, provided herein are methods for treatment of one or more symptoms of diseases or conditions associated with CRTH2 receptor activity, including, but not limited to an allergic disease, an eosinophil-related disease, a basophil-related disease, or an inflammatory disease. In other embodiments, provided herein are methods for treating a disease or condition, or symptom thereof, wherein the disease or condition is selected from the group consisting of asthma, exercise induced asthma, allergic rhinitis, atopic dermatitis, allergic conjunctivitis, Churg-Strauss syndrome, sinusitis, basophilic leukemia, chronic urticaria, basophilic leukocytosis, psoriasis, eczema, inflammatory bowel disease, ulcerative colitis, Crohn's disease, COPD (chronic obstructive pulmonary disorder) and arthritis.

DETAILED DESCRIPTION

Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutically acceptable salts of the compounds provided herein also include the acid and base salts thereof.

Suitable acid salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see *Handbook of Pharmaceutical Salts: Properties, Selection, and Use* by Stahl and Wermuth (Wiley-VCH, 2002).

Pharmaceutically acceptable esters include, but are not limited to, alkyl, alkenyl, alkynyl, aryl, aralkyl and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of the formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, aralkyl or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, the term "solvate" describes a molecular complex comprising the compound of the invention and one or more pharmaceutically acceptable solvent molecules, for example, ethanol. The term "hydrate" is employed when said solvent is water.

As used herein, treatment means any manner in which one or more of the symptoms of a disease or disorder are ameliorated or otherwise beneficially altered. Treatment also encompasses any pharmaceutical use of the compositions herein, such as use for treating a CTRH2 mediated disease or disorder, or diseases or disorders, in which CRTH2 activity is implicated.

As used herein, $IC_{50}$ refers to an amount, concentration or dosage of a particular test compound that achieves a 50% inhibition of a maximal response, such as modulation of CRTH2 activity, in an assay that measures such response.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified, the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the D- and L-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the term "in combination with" means the administration of a compound provided herein with one or more therapeutic agents either simultaneously, concurrently or sequentially with no specific time limits. In one embodiment, the compound provided herein and the additional agent or agents are present in the cell or in the subject's body at the same time or exert their biological or therapeutic effect at the same time. In one embodiment, the compound provided herein and the additional agent or agents are in the same composition or unit dosage form. In another embodiment, the compound provided herein and the additional agent or agents are in separate compositions or unit dosage forms. In some embodiments, a first compound or agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second compound or agent.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.

As used herein, "sulfonyl" refers to —S(O)$_2$—.

As used herein, "sulfamoyl" refers to —S(O)$_2$NR$_2$ in which each R is independently hydrogen, aryl or alkyl, including lower alkyl.

As used herein, "carboxy" refers to —C(O)OH.

As used herein, "aminocarbonyl" or "carbamoyl" refers to —C(O)NH$_2$.

As used herein, "alkylaminocarbonyl" or "alkylcarbamoyl" refers to —C(O)NHR in which R is alkyl, including lower alkyl.

As used herein, "dialkylaminocarbonyl" or "dialkylcarbamoyl" refers to —C(O)NR'R in which R' and R are independently alkyl, including lower alkyl; "carboxamide" refers to groups of formula —NR'COR in which R' and R are independently alkyl, including lower alkyl.

As used herein, "cycloalkylaminocarbonyl" or "cycloalkylcarbamoyl" refers to —C(O)NHR in which R is cycloalkyl.

As used herein, "heterocyclylaminocarbonyl" or "heterocyclylcarbamoyl" refers to —C(O)NHR in which R is heterocyclyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

Where the number of any given substituent is not specified (e.g., haloalkyl), there may be one or more substituents present. For example, "haloalkyl" may include one or more of the same or different halogens. As another example, "C$_{1-3}$ alkoxyphenyl" may include one or more of the same or different alkoxy groups containing one, two or three carbons.

As used herein, "alkyl," "alkenyl," "alkynyl," "cycloalkyl," "aryl," "heteroaryl," "heterocyclyl," "aralkyl," "heteroaralkyl," "haloalkyl," "haloalkoxy," "carboxy," "aminocarbonyl," "carbamoyl," "alkylaminocarbonyl," "alkylcarbamoyl," "dialkylaminocarbonyl," "dialkylcarbamoyl," "cycloalkylaminocarbonyl," "cycloalkylcarbamoyl," "heterocyclylaminocarbonyl," "heterocyclylcarbamoyl," "alkoxy," "alkylthio," "aryloxy," "arylthio," "alkylene," "amido," "thioamido," "oxyamido," "thiaamido," "dithiaamido," "ureido" and "thioureido" groups optionally comprise deuterium at one or more positions where hydrogen atoms are present, and wherein the deuterium composition of the atom or atoms is other than the natural isotopic composition.

Also as used herein, "alkyl," "alkenyl," "alkynyl," "cycloalkyl," "aryl," "heteroaryl," "heterocyclyl," "alkyl," "alkenyl," "alkynyl," "cycloalkyl," "aryl," "heteroaryl," "heterocyclyl," "aralkyl," "heteroaralkyl," "haloalkyl," "haloalkoxy," "carboxy," "aminocarbonyl," "carbamoyl," "alkylaminocarbonyl," "alkylcarbamoyl," "dialkylaminocarbonyl," "dialkylcarbamoyl," "cycloalkylaminocarbonyl," "cycloalkylcarbamoyl," "heterocyclylaminocarbonyl," "heterocyclylcarbamoyl," "alkoxy," "alkylthio," "aryloxy," "arylthio," "alkylene," "amido," "thioamido," "oxyamido," "thiaamido," "dithiaamido," "ureido" and "thioureido" groups optionally comprise carbon-13 at an amount other than the natural isotopic composition.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

Compounds

In certain embodiments, the compounds for use in the compositions and methods provided herein have Formula I:

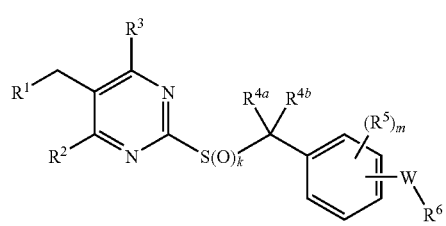

or a pharmaceutically acceptable salt, solvate, hydrate, stereoisomer or tautomer thereof, wherein $R^1$ is —CO$_2$R$^9$, —C(O)NR$^{8a}$R$^{8b}$, (nitrile or tetrazolyl;

$R^{4a}$ and $R^{4b}$ are each independently hydrogen or (C$_1$-C$_6$) alkyl;

in each instance, independently, W, $R^2$, $R^3$, $R^5$, $R^{5a}$, $R^6$, $R^7$, $R^{8a}$, $R^{8b}$, $R^9$, $R^{10}$, $R^{11}$, $R^{12}$, $R^{13}$, $R^{14}$, $R^{15}$, m and n are selected from (I) or (II) as follows:

(I) W is a single bond, —(CH$_2$)$_m$—, —O—, —S(O)$_n$—, —NR$^7$—, —C(O)—, —C(O)O—, —C(O)NR$^7$—, —NR$^7$C(O)NR$^7$— or —NR$^7$C(O)O—;

in each instance, independently, $R^2$ and $R^3$ are selected from (i) or (ii) as follows:

(i) $R^2$ and $R^3$ are each independently (a) hydrogen; (b) F; (c) Br; (d) I; (e) (C$_1$-C$_6$)alkyl; (f) (C$_1$-C$_6$)alkyl substituted by aryl, hydroxy, carboxy, alkoxy, carbamoyl, (C$_1$-C$_6$)alkylcarbamoyl, di(C$_1$-C$_6$)alkyl)carbamoyl, (C$_3$-C$_7$)cycloalkylcarbamoyl or (C$_3$-C$_7$)heterocyclylcarbamoyl; (g) (C$_1$-C$_6$)alkyl substituted by mono-, di-, or tri-halogen; (h) (C$_3$-C$_7$)cycloalkyl; (i) —SR$^9$; (j) —NR$^{10}$R$^{11}$; or (k) (C$_1$-C$_6$)alkoxy optionally substituted by mono-, di-, or tri-halogen; or (ii) $R^2$ and $R^3$ are each independently (a) hydrogen; (b) Cl; (c) (C$_1$-C$_6$)alkyl; (d) (C$_1$-C$_6$)alkyl substituted by aryl, hydroxy, carboxy, alkoxy, carbamoyl, (C$_1$-C$_6$)alkylcarbamoyl, di(C$_1$-C$_6$)alkyl)carbamoyl, (C$_3$-C$_7$)cycloalkylcarbamoyl or (C$_3$-C$_7$)heterocyclylcarbamoyl; (e) (C$_1$-C$_6$)alkyl substituted by mono-, di-, or tri-halogen; (f) (C$_3$-C$_7$)cycloalkyl; (g) —SR$^9$; (h) —NR$^{12}$R$^{13}$; or (i) (C$_1$-C$_6$) alkoxy optionally substituted by mono-, di-, or tri-halogen;

$R^5$ is (a) hydrogen; (b) halogen; (c) cyano; (d) nitro; (e) hydroxy; (f) phenyl; (g) phenyloxy; (h) benzyl; (i) benzyloxy; (j) guanidino; (k) heterocyclyl; (l) —NR$^{14}$R$^{15}$; (m) sulfamoyl; (n) (C$_1$-C$_6$)alkylsulfonyl; (O) (C$_1$-C$_6$)alkylaminosulfonyl; (p) di(C$_1$-C$_6$) alkylaminosulfonyl; (q) —C(O)R$^9$; (r) —C(O)OR$^9$; (s) —C(O)NR$^{8a}$R$^{8b}$; (t) —NR$^7$C(O)R$^9$; (u) —OC(O)NR$^{8a}$R$^{8b}$; (v) —NR$^7$C(O)OR$^9$; (w) (C$_2$-C$_6$)alkenyl; (x) (C$_1$-C$_6$)alkyl optionally substituted by mono-, di-, or tri-halogen; (y) (C$_1$-C$_6$)alkoxy optionally substituted by mono-, di-, or tri-halogen; or (z) $(C_1-C_6)$alkylthio optionally substituted by mono-, di-, or tri-halogen;

$R^6$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkyl substituted by mono-, di-, or tri-halogen; (i) $(C_1-C_6)$alkyl substituted by —C(O)$R^{6a}$; (j) $(C_1-C_6)$alkoxy substituted by mono-, di-, or tri-halogen; (k) $(C_1-C_6)$alkylthio substituted by mono-, di-, or tri-halogen; (l) aryl; (m) or heteroaryl, wherein said aryl and heteroaryl are optionally substituted at a substitutable position with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —$NR^{8a}R^{8b}$; (l) —C(O)$R^9$; (m) —C(O)$NR^{8a}R^{8b}$; (n) —OC(O)$NR^{8a}R^{8b}$; (O) —C(O)$OR^9$; (p) —$NR^7C(O)OR^9$; (q) —$NR^7C(O)R^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^{6a}$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkyl substituted by mono-, di-, or tri-halogen; (i) $(C_1-C_6)$alkoxy substituted by mono-, di-, or tri-halogen; (j) $(C_1-C_6)$alkylthio substituted by mono-, di-, or tri-halogen; (k) aryl; (l) or heteroaryl, wherein said aryl and heteroaryl are optionally substituted at a substitutable position with one or more substituents selected from the group consisting of (a) halogen; (b) cyano; (c) nitro; (d) hydroxy; (e) guanidino; (0 heterocyclyl; (g) phenyl; (h) phenyloxy; (i) benzyl; (j) benzyloxy; (k) —$NR^{8a}R^{8b}$; (l) —C(O)$R^9$; (m) —C(O)$NR^{8a}R^{8b}$; (n) —OC(O)$NR^{8a}R^{8b}$; (o) —C(O)$OR^9$; (p) —$NR^7C(O)OR^9$; (q) —$NR^7C(O)R^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^7$ is (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl;

in each instance, independently, $R^{8a}$ and $R^{8b}$ are selected from (i) or (ii) as follows:
 (i) $R^{8a}$ and $R^{8b}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
 (ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

each $R^9$ is independently (a) hydrogen; (b) $(C_1-C_6)$alkyl; phenyl; or (c) $(C_1-C_6)$alkyl substituted by aryl, alkoxy or mono-, di-, or tri-halogen;

in each instance, independently, $R^{10}$ and $R^{11}$ are selected from (i) or (ii) as follows:
 (i) $R^{10}$ and $R^{11}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
 (ii) each $R^{10}$ and $R^{11}$, together with the N to which they are bonded, independently may form a 3 to 8 membered saturated or unsaturated ring optionally containing one or more O or S atoms, or one or more additional N atoms, in the ring;

in each instance, independently, $R^{12}$ and $R^{13}$ are selected from (i), (ii), (iii) or (iv) as follows:
 (i) $R^{12}$ and $R^{13}$ are each independently selected from (a) hydrogen; (b) $(C_1-C_6)$alkyl; (c) phenyl; (d) $(C_1-C_6)$alkyl substituted by aryl, hydroxy, carboxy or alkoxy; (e) $(C_1-C_6)$alkyl substituted by mono-, di-, or tri-halogen; or (t) $(C_3-C_7)$cycloalkyl;
 (ii) $R^{12}$ and $R^{13}$, together with the N to which they are bonded, form a 5 membered saturated ring containing at least one O or S atom, or at least one additional N atom, in the ring;
 (iii)$R^{12}$ and $R^{13}$, together with the N to which they are bonded, form a 5 membered unsaturated ring, optionally containing one or more O or S atom, or one or more additional N atoms, in the ring; or
 (iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring;

in each instance, independently, $R^{14}$ and $R^{15}$ are selected from (i) or (ii) as follows:
 (i) $R^{14}$ and $R^{15}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
 (ii) each $R^{14}$ and $R^{15}$, together with the N to which they are bonded, independently may form a 3 to 8 membered saturated or unsaturated ring optionally containing one or more O or S atoms, or one or more additional N atoms, in the ring;

k is 0, 1 or 2;
m is 1, 2, 3 or 4;
n is 0, 1 or 2; or
(II) $R^5$ and W—$R^6$ together with the atom to which they are attached may form a 4 to 8 membered unsaturated ring optionally containing one or more N, O or S atoms in the ring, wherein the ring is optionally substituted with one or more $R^{5a}$ groups;

$R^2$ and $R^3$ are each independently (a) hydrogen; (b) F; (c) (d) Br; (e) I; (f) $(C_1-C_6)$alkyl; (g) $(C_1-C_6)$alkyl substituted by aryl, hydroxy, carboxy, alkoxy, carbamoyl, $(C_1-C_6)$alkylcarbamoyl, di$(C_1-C_6)$alkyl)carbamoyl, $(C_3-C_7)$cycloalkylcarbamoyl or $(C_3-C_7)$heterocyclylcarbamoyl; (h) $(C_1-C_6)$alkyl substituted by mono-, di-, or tri-halogen; (i) $(C_3-C_7)$cycloalkyl; (j) —$SR^9$; (k) —$NR^{10}R^{11}$; or (l) $(C_1-C_6)$alkoxy optionally substituted by mono-, di-, or tri-halogen;

$R^5$ and $R^{5a}$ are each independently (a) hydrogen; (b) halogen; (c) cyano; (d) nitro; (e) hydroxy; (l) phenyl; (g) phenyloxy; (h) benzyl; (i) benzyloxy; (j) guanidino; (k) heterocyclyl; (l) —$NR^{14}R^{15}$; (m) sulfamoyl; (n) $(C_1-C_6)$alkylsulfonyl; (o) $(C_1-C_6)$alkylaminosulfonyl; (p) di$(C_1-C_6)$alkylaminosulfonyl; (q) —$C(O)R^9$; (r) —$C(O)OR^9$; (s) —$C(O)NR^{8a}R^{8b}$; (t) —$NR^7C(O)R^9$; (u) —$OC(O)NR^{8a}R^{8b}$; (v) —$NR^7C(O)OR^9$; (w) $(C_2-C_6)$alkenyl; (x) $(C_1-C_6)$alkyl optionally substituted by mono-, di-, or tri-halogen; (y) $(C_1-C_6)$alkoxy optionally substituted by mono-, di-, or tri-halogen; or (z) $(C_1-C_6)$alkylthio optionally substituted by mono-, di-, or tri-halogen;

$R^6$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkyl substituted by mono-, di-, or tri-halogen; (i) $(C_1-C_6)$alkyl substituted by —$C(O)R^{6a}$; (j) $(C_1-C_6)$alkoxy substituted by mono-, di-, or tri-halogen; (k) $(C_1-C_6)$alkylthio substituted by mono-, di-, or tri-halogen; (l) aryl; (m) or heteroaryl, wherein said aryl and heteroaryl are optionally substituted at a substitutable position with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —$NR^{8a}R^{8b}$; (l) —$C(O)R^9$; (m) —$C(O)NR^{8a}R^{8b}$; (n) —$OC(O)NR^{8a}R^{8b}$; (o) —$C(O)OR^9$; (p) —$NR^7C(O)OR^9$; (q) —$NR^7C(O)R^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^{6a}$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkyl substituted by mono-, di-, or tri-halogen; (i) $(C_1-C_6)$alkoxy substituted by mono-, di-, or tri-halogen; (j) $(C_1-C_6)$alkylthio substituted by mono-, di-, or tri-halogen; (k) aryl; (l) or heteroaryl, wherein said aryl and heteroaryl are optionally substituted at a substitutable position with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —$NR^{8a}R^{8b}$; (l) —$C(O)R^9$; (m) —$C(O)NR^{8a}R^{8b}$; (n) —$OC(O)NR^{8a}R^{8b}$; (o) —$C(O)OR^9$; (p) —$NR^7C(O)OR^9$; (q) —$NR^7C(O)R^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^7$ is (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl;

in each instance, independently, $R^{8a}$ and $R^{8b}$ are selected from (i) or (ii) as follows:
  (i) $R^{8a}$ and $R^{8b}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
  (ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

each $R^9$ is independently (a) hydrogen; (b) $(C_1-C_6)$alkyl; phenyl; or (c) $(C_1-C_6)$alkyl substituted by aryl, alkoxy or mono-, di-, or tri-halogen;

in each instance, independently, $R^{10}$ and $R^{11}$ are selected from (i) or (ii) as follows:
  (i) $R^{10}$ and $R^{11}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
  (ii) each $R^{10}$ and $R^{11}$, together with the N to which they are bonded, independently may form a 3 to 8 membered saturated or unsaturated ring optionally containing one or more O or S atoms, or one or more additional N atoms, in the ring;

k is 0, 1 or 2;
m is 1, 2, 3 or 4; and
n is 0, 1 or 2.

In one embodiment, in each instance, independently, $R^{10}$ and $R^{11}$ are selected from (i) or (ii) as follows:
  (i) $R^{10}$ and $R^{11}$ are each independently selected from (a) hydrogen; (b) $(C_1-C_6)$alkyl; (c) phenyl; (d) $(C_1-C_6)$alkyl substituted by unsubstituted phenyl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
  (ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and in each instance, independently, $R^{12}$ and $R^{13}$ are selected from (i), (ii), (iii) or (iv) as follows:
(i) $R^{12}$ and $R^{13}$ are each independently selected from (a) hydrogen; (b) $(C_1-C_6)$alkyl; (c) phenyl; (d) $(C_1-C_6)$alkyl substituted by unsubstituted phenyl, hydroxy, carboxy or alkoxy; (e) $(C_1-C_6)$alkyl substituted by mono-, di-, or tri-halogen; or (f) $(C_3-C_7)$cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more O or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

In another embodiment, in each instance, independently, $R^{10}$ and $R^{11}$ are selected from (i) or (ii) as follows:
(i) $R^{10}$ and $R^{11}$ are each independently selected from (a) hydrogen; (b) $(C_1-C_6)$alkyl; (c) phenyl; (d) $(C_1-C_6)$alkyl substituted by hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and in each instance, independently, $R^{12}$ and $R^{13}$ are selected from (i), (ii), (iii) or (iv) as follows:
(i) $R^{12}$ and $R^{13}$ are each independently selected from (a) hydrogen; (b) $(C_1-C_6)$alkyl; (c) phenyl; (d) $(C_1-C_6)$alkyl substituted by hydroxy, carboxy or alkoxy; (e) $(C_1-C_6)$alkyl substituted by mono-, di-, or tri-halogen; or (f) $(C_3-C_7)$cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more O or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

In another embodiment, in each instance, independently, $R^{10}$ and $R^{11}$ are selected from (i) or (ii) as follows:
(i) $R^{10}$ and $R^{11}$ are each independently selected from (a) hydrogen; (b) $(C_1-C_6)$alkyl; (c) phenyl; (d) $(C_1-C_6)$alkyl substituted by mono-, di-, or tri-halogen; or (e) $(C_3-C_7)$cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and in each instance, independently, $R^{12}$ and $R^{13}$ are selected from (i), (ii), (iii) or (iv) as follows:
(i) $R^{12}$ and $R^{13}$ are each independently selected from (a) hydrogen; (b) $(C_1-C_6)$alkyl; (c) phenyl; (d) $(C_1-C_6)$alkyl substituted by mono-, di-, or tri-halogen; or (e) $(C_3-C_7)$cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more O or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

In one embodiment, $R^1$ is —CO$_2$H.

In another embodiment, $R^{4a}$ and $R^{4b}$ are each independently hydrogen.

In another embodiment, the compounds have formula II:

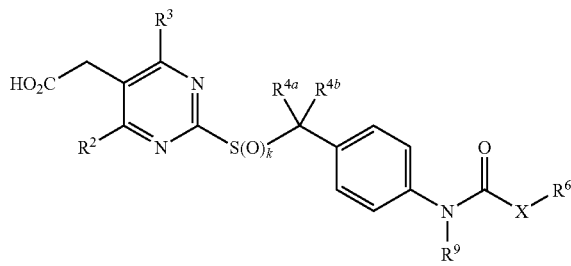

or a pharmaceutically acceptable salt, solvate, hydrate, stereoisomer or tautomer thereof, wherein
X is a single bond, —O(CH$_2$)$_p$— or —NR$^9$(CH$_2$)$_p$—;
$R^9$ is hydrogen or $(C_1-C_6)$alkyl; and
p is 1, 2, 3, 4, 5 or 6.

In certain embodiments, $R^2$ is halogen.

In certain embodiments, $R^{4a}$ and $R^{4b}$ are each independently hydrogen.

In another embodiment, $R^6$ is aryl or heteroaryl, wherein said aryl and heteroaryl are optionally substituted at a substitutable position with one or more substituents selected from the group consisting of (a) halogen; (b) cyano; (c) nitro; (d) hydroxy; (e) —NR$^{14}$R$^{15}$; (f) —C(O)R$^9$; (g) —C(O)NR$^{8a}$R$^{8b}$; (h) —NR$^7$C(O)R$^9$; (i) —OC(O)NR$^{8a}$R$^{8b}$; (j) —NR$^7$C(O)OR$^9$; (k) —C(O)OR$^9$; (l) guanidino; (m) heterocyclyl; (n) phenyl; (o) phenyloxy; (p) benzyl; (q) benzyloxy; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^7$ is hydrogen or $(C_1-C_6)$alkyl;

in each instance, independently, $R^{8a}$ and $R^{8b}$ are selected from (i) or (ii) as follows:
(i) $R^{8a}$ and $R^{8b}$, are each independently selected from hydrogen or $(C_1-C_6)$alkyl; or
(ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

in each instance, independently, $R^{14}$ and $R^{15}$ are selected from (i) or (ii) as follows:
- (i) $R^{14}$ and $R^{15}$ are each independently selected from (a) hydrogen; (b) $(C_1-C_6)$alkyl; (c) phenyl; (d) $(C_1-C_6)$alkyl substituted by aryl, hydroxy, carboxy or alkoxy; (e) $(C_1-C_6)$alkyl substituted by mono-, di-, or tri-halogen; or (f) $(C_3-C_7)$cycloalkyl; or
- (ii) each $R^{14}$ and $R^{15}$, together with the N to which they are bonded, independently may form a 3 to 8 membered saturated or unsaturated ring optionally containing one or more O or S atoms, or one or more additional N atoms, in the ring.

In one embodiment, the compounds for use in the compositions and methods provided herein have Formula III:

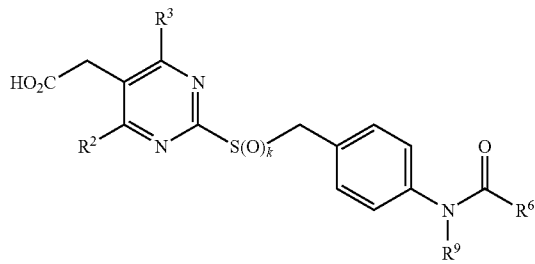

III or a pharmaceutically acceptable salt, solvate, hydrate, stereoisomer or tautomer thereof, wherein $R^9$ is hydrogen.

In another embodiment, $R^6$ is aryl or heteroaryl, wherein said aryl and heteroaryl are optionally substituted at a substitutable position with one or more substituents selected from the group consisting of (a) halogen; (b) cyano; (c) nitro; (d) hydroxy;
- (e) $-NR^{14}R^{15}$; (f) $-C(O)R^9$; (g) $-C(O)NR^{8a}R^{8b}$; (h) $-NR^7C(O)R^9$; (i) $-OC(O)NR^{8a}R^{8b}$; (j) $-NR^7C(O)OR^9$; (k) $-C(O)OR^9$; (l) guanidino; (m) heterocyclyl; (n) phenyl; (o) phenyloxy; (p) benzyl; (q) benzyloxy; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

$R^7$ is hydrogen or $(C_1-C_6)$alkyl;

in each instance, independently, $R^{8a}$ and $R^{8b}$ are selected from (i) or (ii) as follows:
- (i) $R^{8a}$ and $R^{8b}$ are each independently selected from hydrogen or $(C_1-C_6)$alkyl; or
- (ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

in each instance, independently, $R^{14}$ and $R^{15}$ are selected from (i) or (ii) as follows:
- (i) $R^{14}$ and $R^{15}$ are each independently selected from (a) hydrogen; (b) $(C_1-C_6)$alkyl; (c) phenyl; (d) $(C_1-C_6)$alkyl substituted by aryl, hydroxy, carboxy or alkoxy; (e) $(C_1-C_6)$alkyl substituted by mono-, di-, or tri-halogen; or (f) $(C_3-C_7)$cycloalkyl; or
- (ii) each $R^{14}$ and $R^{15}$, together with the N to which they are bonded, independently may form a 3 to 8 membered saturated or unsaturated ring optionally containing one or more O or S atoms, or one or more additional N atoms, in the ring.

In certain embodiments, $R^2$ and $R^3$ are each $-N(CH_3)_2$.

In one embodiment, the compounds for use in the compositions and methods provided herein have formula IV:

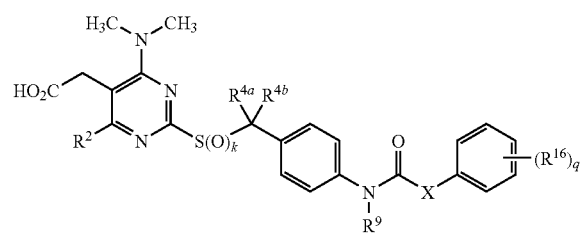

IV or a pharmaceutically acceptable salt, solvate, hydrate, stereoisomer or tautomer thereof, wherein $R^2$ is halogen;

each $R^{16}$ is independently (a) hydrogen (b) halogen; (c) cyano; (d) nitro; (e) hydroxy; (f) $-NR^{14}R^{15}$; (g) $-C(O)R^9$; (h) $-C(O)NR^{8a}R^{8b}$; (i) $-NR^7C(O)R^9$; (j) $-OC(O)NR^{8a}R^{8b}$; (k) $-NR^7C(O)OR^9$; (l) $-C(O)OR^9$; (m) guanidino; (n) heterocyclyl; (o) phenyl; (p) phenyloxy; (q) benzyl; (r) benzyloxy; (s) sulfamoyl; (t) $(C_1-C_6)$alkylsulfonyl; (u) $(C_1-C_6)$alkylaminosulfonyl; (v) di$(C_1-C_6)$alkylaminosulfonyl; (w) $(C_1-C_6)$alkyl optionally substituted by mono-, di-, or tri-halogen; (x) $(C_1-C_6)$alkoxy optionally substituted by mono-, di-, or tri-halogen; and (y) $(C_1-C_6)$alkylthio optionally substituted by mono-, di-, or tri-halogen; and q is 0, 1, 2, 3, 4 or 5.

In certain embodiments, each $R^{16}$ is independently (a) hydrogen (b) halogen; (c) cyano; (d) nitro; (e) hydroxy; (f) $-NH_2$; (g) $-NH(C_1-C_6)$alkyl; (h) $-N((C_1-C_6)$alkyl$)_2$; (i) $-NHC(O)(C_1-C_6)$alkyl; (j) $-C(O)(C_1-C_6)$alkyl; (k) $-CO_2H$; (l) $-C(O)O(C_1-C_6)$alkyl; (m) phenyl; (n) phenyloxy; (o) benzyl; (p) benzyloxy; (q) sulfamoyl; (r) $(C_1-C_6)$alkylsulfonyl; (s) $(C_1-C_6)$alkylaminosulfonyl; (t) di$(C_1-C_6)$alkylaminosulfonyl; (u) $(C_1-C_6)$alkyl optionally substituted by mono-, di-, or tri-halogen; (v) $(C_1-C_6)$alkoxy optionally substituted by mono-, di-, or tri-halogen; or (w) $(C_1-C_6)$alkylthio optionally substituted by mono-, di-, or tri-halogen.

In one embodiment, the compounds for use in the compositions and methods provided herein have formula V:

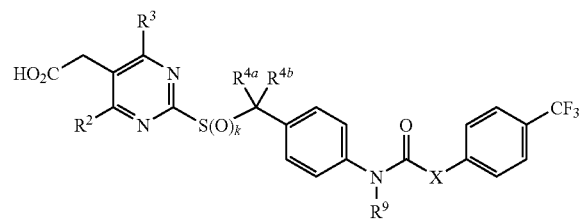

V or a pharmaceutically acceptable salt, solvate, hydrate, stereoisomer or tautomer thereof.

In certain embodiments, $R^2$ is halogen.

In certain embodiments, $R^2$ is halogen and $R^3$ is $-N(CH_3)_2$.

In another embodiment, $R^2$ and $R^3$ are each independently —N(CH$_3$)$_2$.

In one embodiment, the compound has formula:

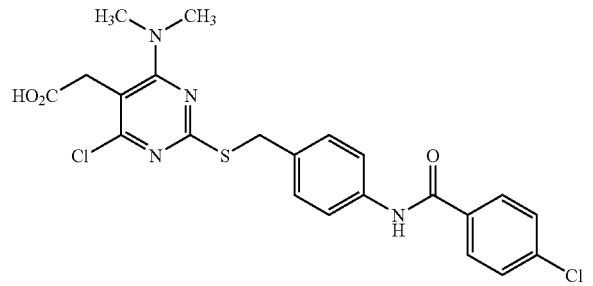

In another embodiment, the compound has formula:

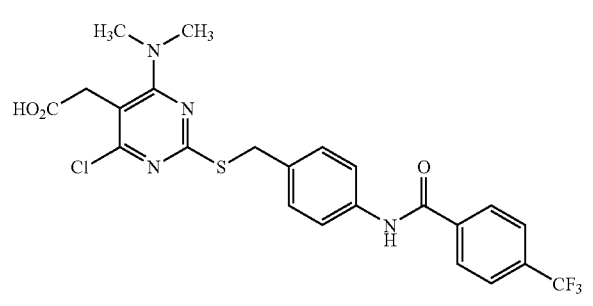

In another embodiment, the compound has formula:

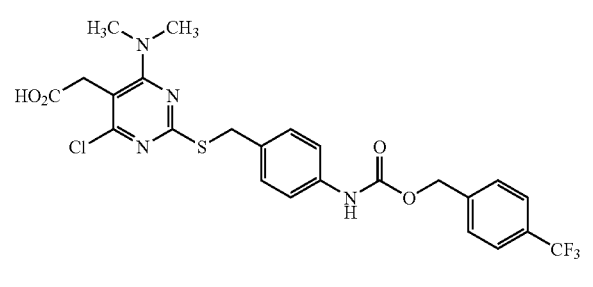

In another embodiment, the compound has formula:

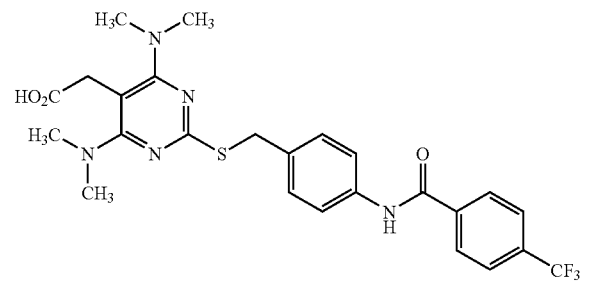

In another embodiment, the compound has formula:

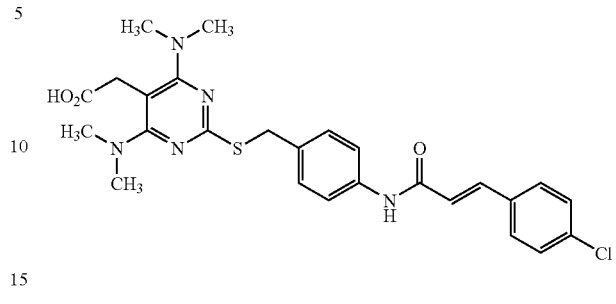

In another embodiment, the compound has formula:

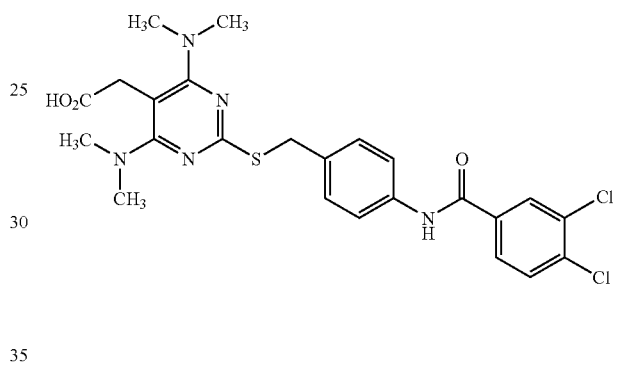

In another embodiment, the compound has formula:

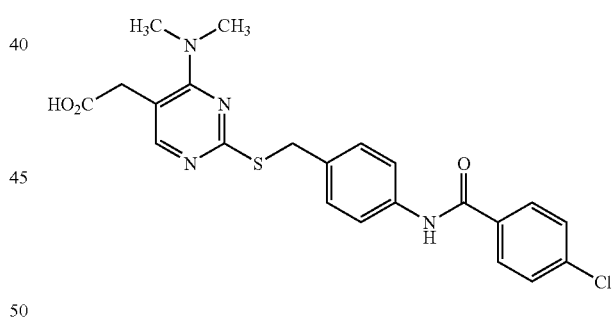

In another embodiment, the compound has formula:

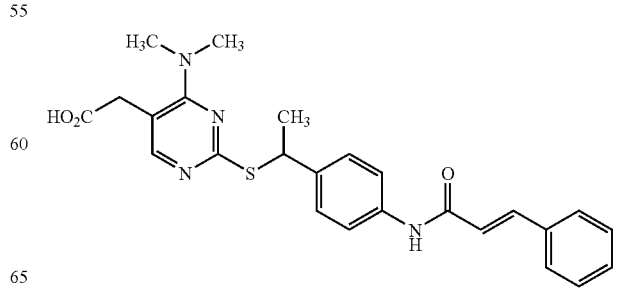

In another embodiment, the compound has formula:

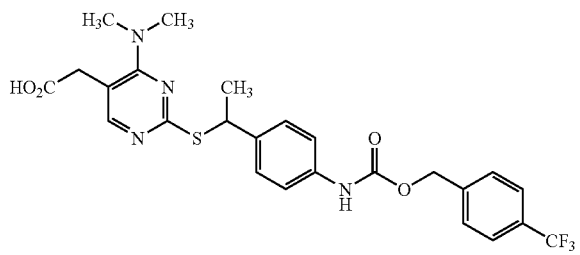

In another embodiment, the compound has formula:

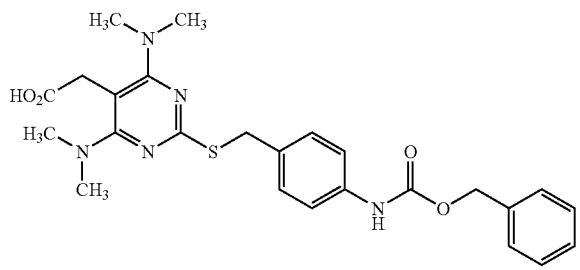

In another embodiment, the compound has formula:

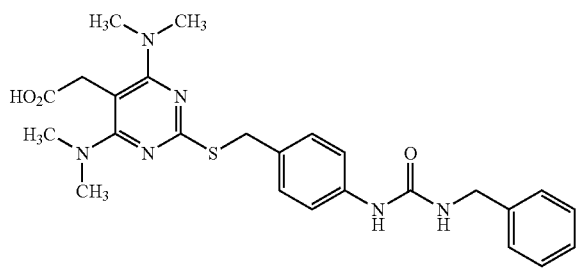

In another embodiment, the compounds for use in the compositions and methods provided herein have formula VI

VI

HO$_2$C—[structure with R$^3$, R$^2$, R$^{4a}$, R$^{4b}$, S(O)$_k$, Y, R$^{6a}$]

or a pharmaceutically acceptable salt, solvate, hydrate, stereoisomer or tautomer thereof, wherein
Y is NH, O or S; and
R$^{6a}$ is (a) hydrogen; (b) (C$_1$-C$_6$)alkyl; (c) (C$_2$-C$_6$)alkenyl; (d) (C$_2$-C$_6$)alkynyl; (e) (C$_3$-C$_7$)cycloalkyl; (f) (C$_1$-C$_6$)alkyl substituted by aryl or heteroaryl; (g) (C$_2$-C$_4$)alkenyl substituted by aryl or heteroaryl; (h) (C$_1$-C$_6$)alkyl substituted by mono-, di-, or tri-halogen; (i) (C$_1$-C$_6$)alkoxy substituted by mono-, di-, or tri-halogen; (j) (C$_1$-C$_6$)alkylthio substituted by mono-, di-, or tri-halogen; (k) aryl; or (l) heteroaryl, wherein said aryl and heteroaryl are optionally substituted at a substitutable position with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —NR$^{14}$R$^{15}$; (l) —C(O)R$^9$; (m) —C(O)NR$^{8a}$R$^{8b}$; (n) —OC(O)NR$^{8a}$R$^{8b}$; (m) —NR$^7$C(O)R$^9$; (n) —C(O)OR$^9$; (o) —NR$^7$C(O)OR$^9$; (p) sulfamoyl; (q) (C$_1$-C$_6$)alkylsulfonyl; (r) (C$_1$-C$_6$)alkylaminosulfonyl; (s) di(C$_1$-C$_6$)alkylaminosulfonyl; (t) (C$_1$-C$_6$)alkyl optionally substituted by mono-, di-, or tri-halogen; (u) (C$_1$-C$_6$)alkoxy optionally substituted by mono-, di-, or tri-halogen; and (v) (C$_1$-C$_6$)alkylthio optionally substituted by mono-, di-, or tri-halogen.

The compounds provided herein may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials, when heated sufficiently, will also exhibit the properties of a liquid, but the change from solid to liquid is characterized by a phase change, typically first order ('melting point').

The compounds provided herein may also exist in unsolvated and solvated forms. A solvate form provided herein, for example, include hydrates. A currently accepted classification system for organic hydrates is one that defines isolated site, channel, or metal-ion coordinated hydrates—see *Polymorphism in Pharmaceutical Solids* by K. R. Morris (Ed. H. G. Brittain, CRC, 1999). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of this disclosure are metabolites of the compounds provided herein, that is, compounds formed in vivo upon administration of a compound provided herein. Some examples of metabolites provided herein include (i) where the compound contains a methyl group, an hydroxymethyl derivative thereof (—CH$_3$→—CH$_2$OH):

(ii) where the compound contains an alkoxy group, an hydroxy derivative thereof (—OR→—OH);

(iii) where the compound contains a tertiary amino group, a secondary amino derivative thereof (—NR$^1$R$^2$→—NHR$^1$ or —NHR$^2$);

(iv) where the compound contains a secondary amino group, a primary derivative thereof (—NHR$^1$→—NH$_2$);

(v) where the contains a phenyl moiety, a phenol derivative thereof (—Ph→—PhOH); and (vi) where the compound contains an amide group, a carboxylic acid derivative thereof (—CONH$_2$→COOH).

The compounds provided herein may also contain one or more asymmetric carbon atoms and can exist as two or more stereoisomers. Where a compound provided herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds containing, for example, an imino, keto, or oxime group, or so-called valence tautomerism in compounds which contain an aromatic moiety. It follows that a single compound may exhibit more than one type of isomerism.

Included within the scope of the present disclosure are all stereoisomers, geometric isomers and tautomeric forms of the compounds provided herein, including compounds exhibiting more than one type of isomerism, and mixtures of one or more thereof. Also included are acid or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds provided herein (and chiral precursors thereof) may be obtained in enantiomerically-enriched form using chromatography, typically HPLC, on an asymmetric resin with a mobile phase consisting of a hydrocarbon, including heptane or hexane, containing from 0 to 50% by volume of isopropanol, in one embodiment, from 2% to 20% in another embodiment, and from 0 to 5% by volume of an alkylamine, in one embodiment 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

Also provided herein are isotopically enriched 2-S-benzyl pyrimidine compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as T$_2$O. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of the Compounds

The compounds provided herein are commercially available or can be prepared by routine chemical reactions known to one of skill in the art. General schemes for the preparation of exemplary compounds are illustrated below:

Scheme 1: Preparation of 4-chloro-6-amino-2-S-benzyl substituted pyrimidines.

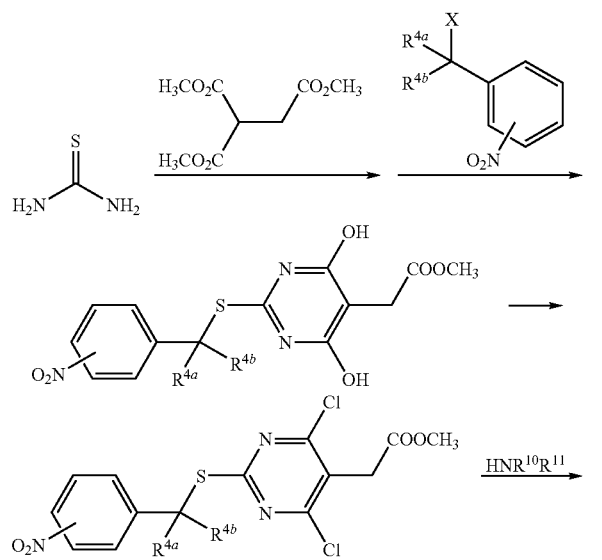

-continued

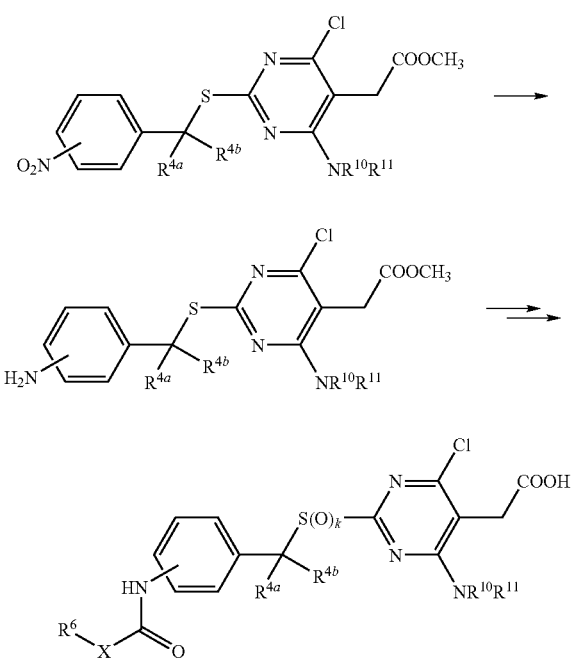

Scheme 2: Preparation of 4, 6-bis-amino-2-S-benzyl substituted pyrimidines.

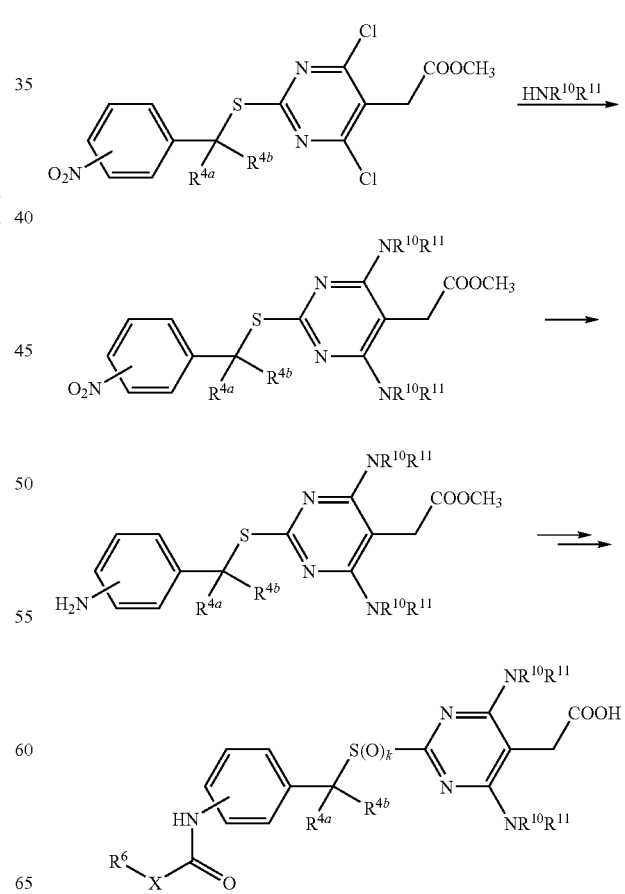

Scheme 3: Preparation of 4-amino-2-S-benzyl and 4-amino-6-alkyl-2-S-benzyl pyrimidines.
Scheme 4: Preparation of 4-amino-6-chloro-2-S-benzoxazolyl pyrimidines.
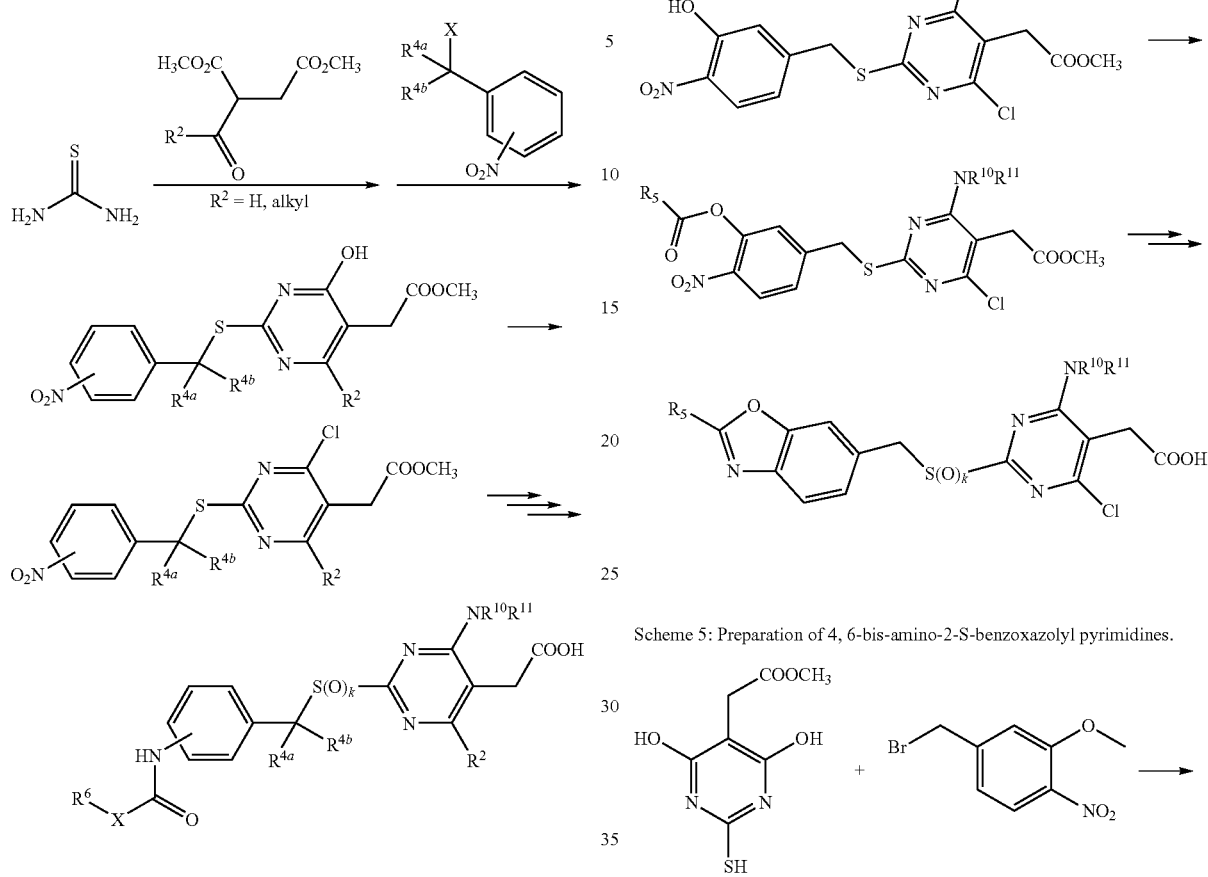
Scheme 5: Preparation of 4, 6-bis-amino-2-S-benzoxazolyl pyrimidines.
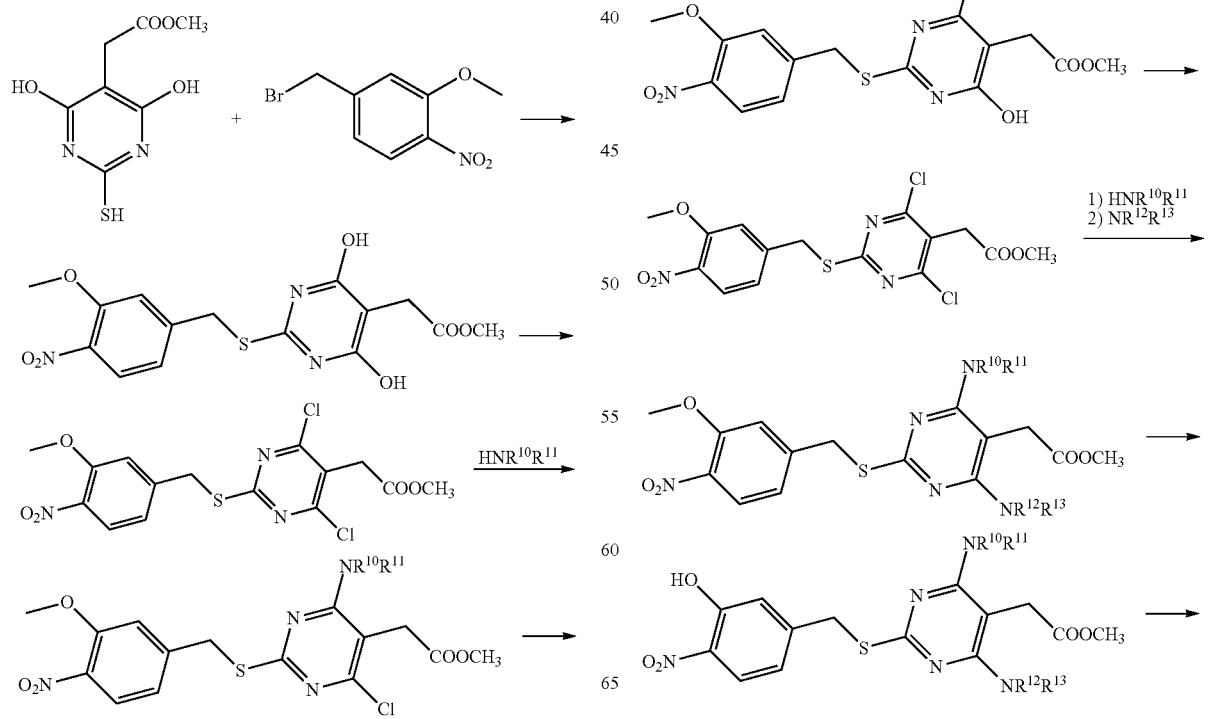

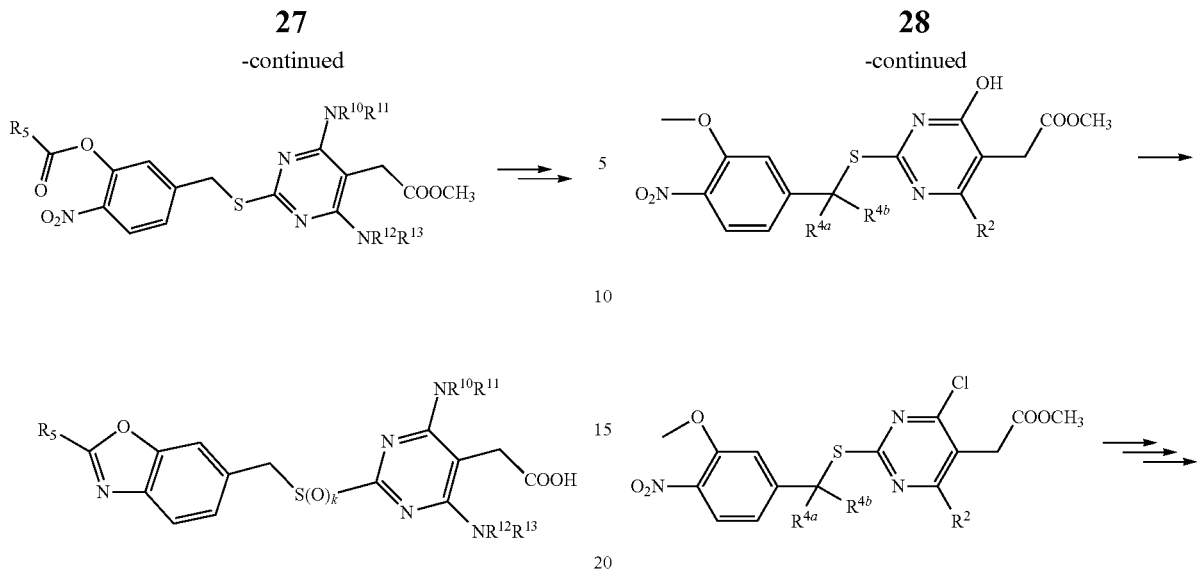
Scheme 6: Preparation of 4-amino-2-S-benzoxazolyl and 4-amino-6-alkyl-2-S-benzoxazolyl pyrimidines.
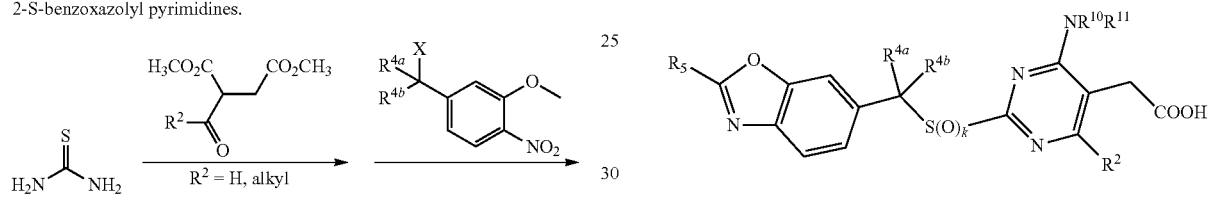
Scheme 7: Preparation of 4-amino-6-chloro-2-benzimidazolyl and 4,6-bis-amino-2-S-benzimidazolyl pyrimidines.
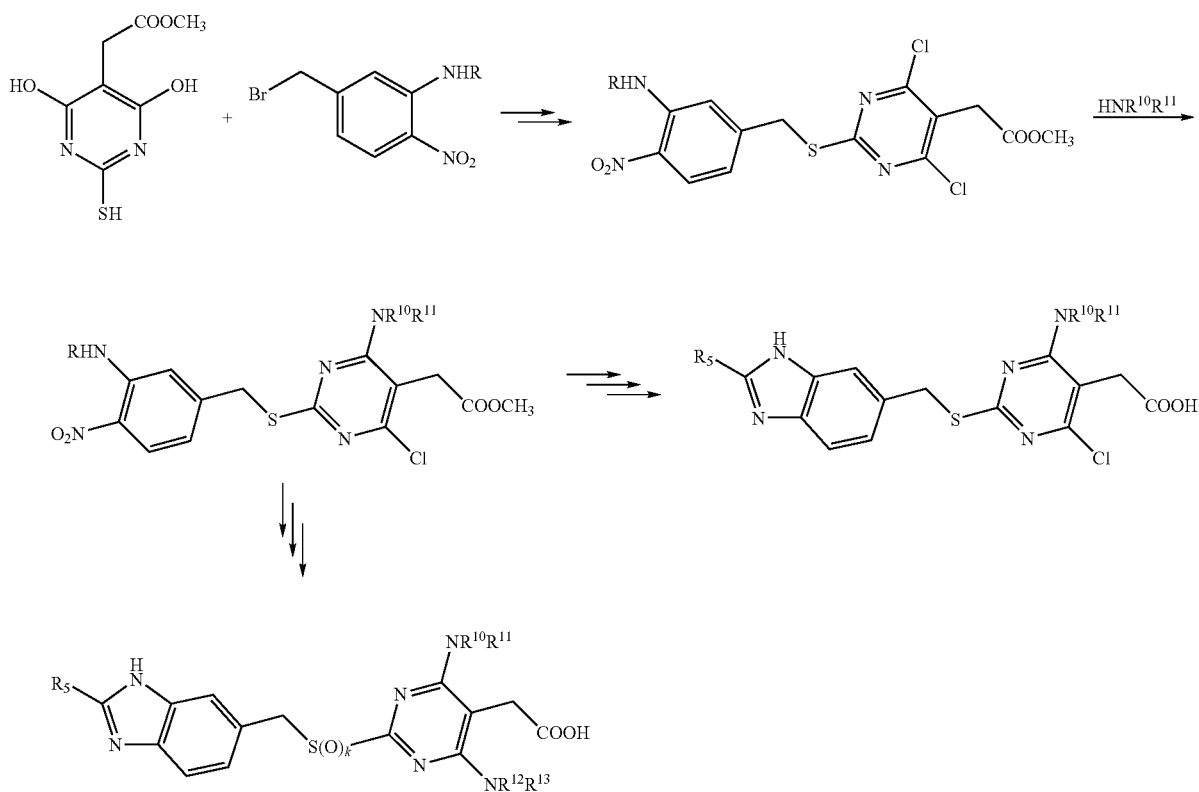

Scheme 8: Preparation of 4-amino-2-S-benzimidazolyl and 4-amino-6-alkyl-2-S-benzimidazolyl pyrimidines.

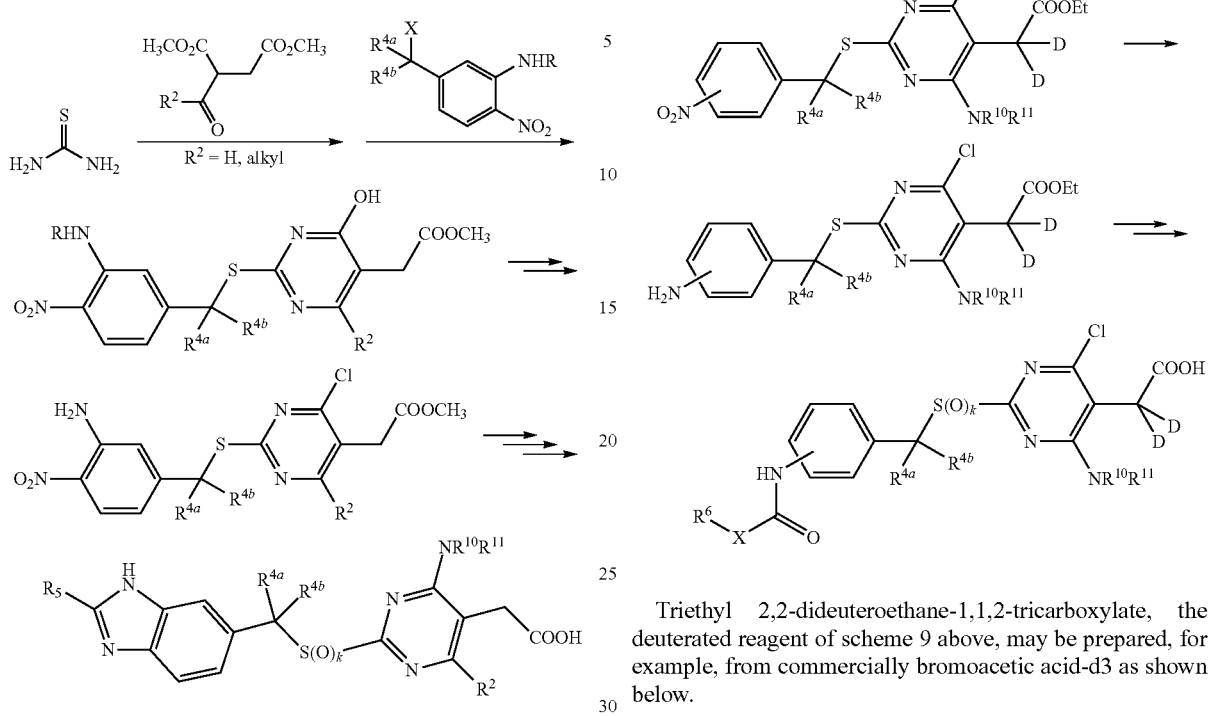

Isotopically enriched analogs of the compounds provided herein may generally be prepared according to the procedures shown above, wherein one or more of the reagents used is replaced by an isotopically enriched reagent. Isotopically enriched reagents are commercially available or may be prepared by routine chemical reactions known to one of skill in the art. General schemes for the preparation of exemplary isotopically enriched compounds are illustrated below.

Scheme 9: Preparation of deuterium analogs.

Triethyl 2,2-dideuteroethane-1,1,2-tricarboxylate, the deuterated reagent of scheme 9 above, may be prepared, for example, from commercially bromoacetic acid-d3 as shown below.

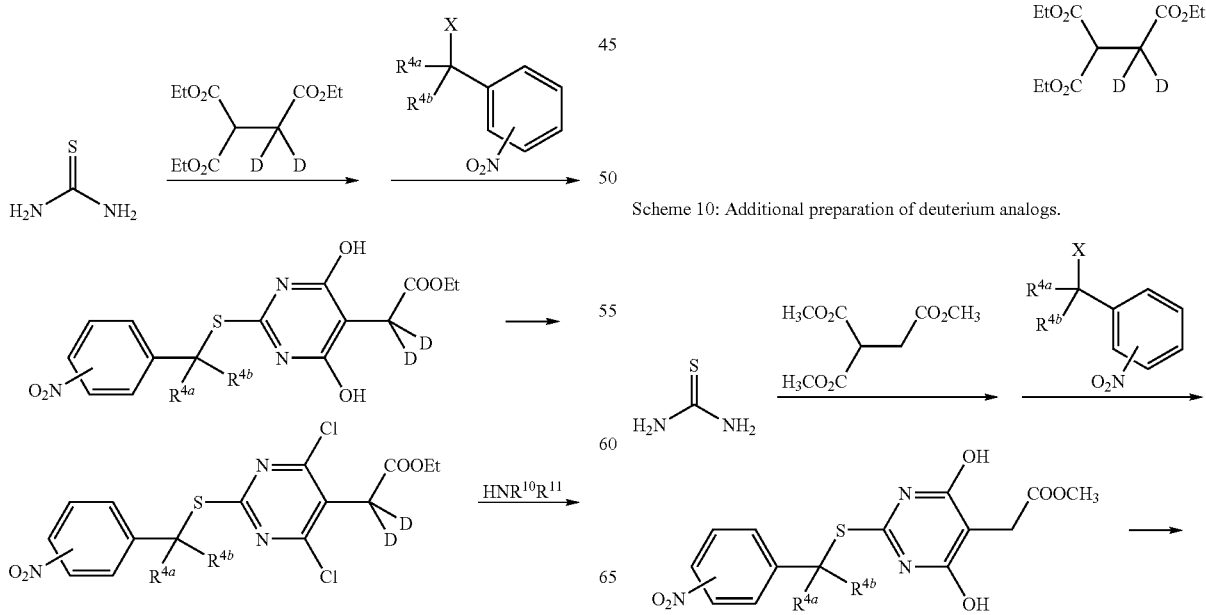

Scheme 10: Additional preparation of deuterium analogs.

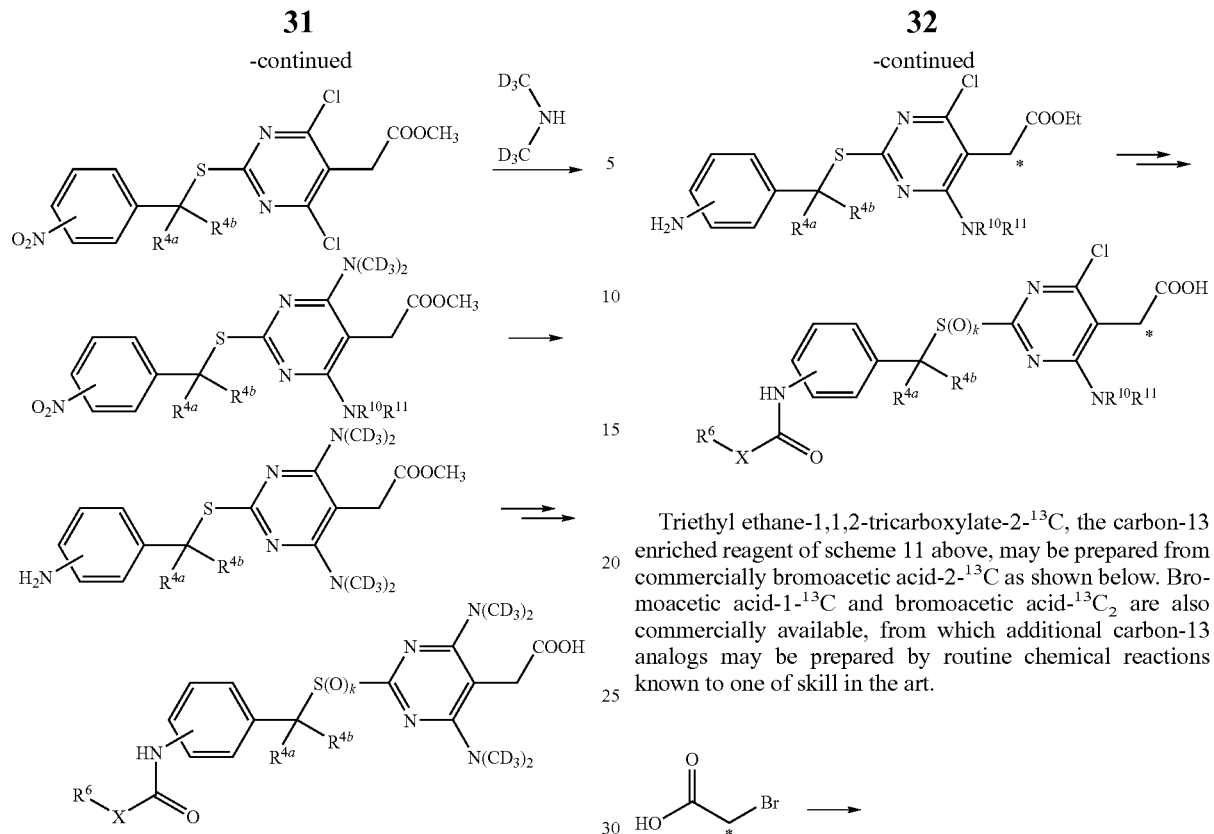

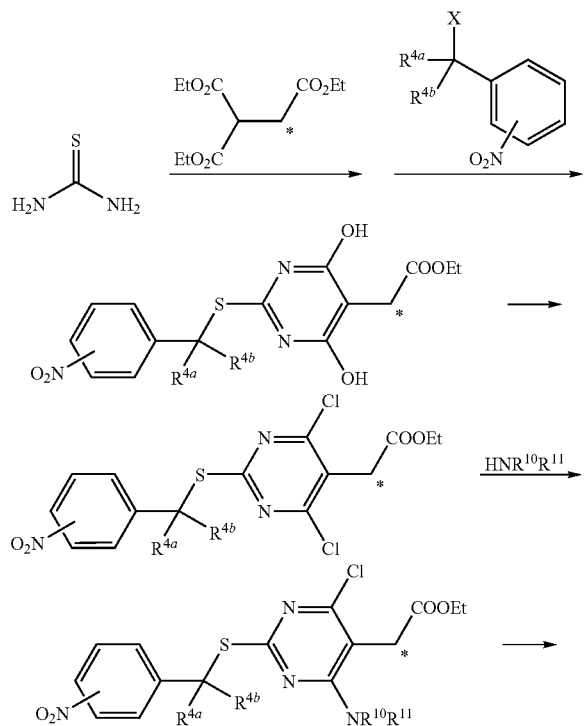

Dimethylamine-d6, the deuterated reagent of scheme 10 above, is commercially available. Other deuterated amines may be purchased or prepared by routine chemical reactions known to one of skill in the art.

Scheme 11: Preparation of carbon-13 analogs.

Triethyl ethane-1,1,2-tricarboxylate-2-$^{13}$C, the carbon-13 enriched reagent of scheme 11 above, may be prepared from commercially bromoacetic acid-2-$^{13}$C as shown below. Bromoacetic acid-1-$^{13}$C and bromoacetic acid-$^{13}$C$_2$ are also commercially available, from which additional carbon-13 analogs may be prepared by routine chemical reactions known to one of skill in the art.

Pharmaceutical Compositions

Also provided herein is a pharmaceutical composition which comprises a compound provided herein, or a pharmaceutically acceptable salt, solvate, hydrate, stereoisomer or tautomer thereof, as an active pharmaceutical ingredient, in combination with one or more pharmaceutically acceptable carriers or excipients. The choice of excipient, to a large extent, depends on factors, such as the particular mode of administration, the effect of the excipient on the solubility and stability of the active ingredient, and the nature of the dosage form.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compounds provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethyleneglycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and $H_2$-receptor antagonists.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral; intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including lard, benzoinated lard, olive oil, cottonseed oil, white petrolatum, and plastibase; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al. in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, Multiparticulate Oral Drug Delivery; Marcel Dekker: 1994; and Pharmaceutical Pelletization Technology; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder or disease associated with CRTH2 and/or one or more other $PGD_2$ receptors by administering to a subject having or being suspected to have such a condition or disease, a therapeutically effective amount of a compound provided herein, or a pharmaceutically acceptable salt, solvate, hydrate, stereoisomer or tautomer thereof; or a pharmaceutical composition thereof.

In another embodiments, provided herein is a method of treating, preventing, or ameliorating one or more symptoms of a disease or disorder responsive to modulation of CRTH2 and/or one or more other $PGD_2$ receptors, comprising administering to a subject having or being suspected to have such a disease or disorder, a therapeutically effective amount of one or more of the compounds or compositions provided herein.

In yet another embodiment, provided herein is a method of treating, preventing, or ameliorating one or more symptoms of a disease or disorder mediated by CRTH2 and/or one or more other $PGD_2$ receptors, comprising administering to a subject having or being suspected to have such a condition or disease, a therapeutically effective amount of one or more of the compounds or compositions provided herein.

In yet another embodiment, provided herein is a method for treating, preventing, or ameliorating one or more symptoms of an eosinophil-related disease, comprising administering to a subject a therapeutically effective amount of a compound provided herein, or a pharmaceutically acceptable salt, solvate, hydrate, stereoisomer or tautomer thereof; or a pharmaceutical composition thereof.

In yet another embodiment, provided herein is a method for treating, preventing, or ameliorating one or more symptoms of a basophil-related disease, comprising administering to a subject a therapeutically effective amount of a compound provided herein, or a pharmaceutically acceptable salt, solvate, hydrate, stereoisomer or tautomer thereof; or a pharmaceutical composition thereof.

In still another embodiment, provided herein is a method for treating, preventing, or ameliorating one or more symptoms of an inflammatory disease, comprising administering to a subject a therapeutically effective amount of a compound provided herein, or a pharmaceutically acceptable salt, solvate, hydrate, stereoisomer or tautomer thereof; or a pharmaceutical composition thereof.

The disorders and diseases treatable with one or more of the compounds provided herein include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disease is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disease is asthma, exercise induced asthma, allergic rhinitis, atopic dermatitis, chronic obstructive plumonary disease, or allergic conjunctivitis.

In certain embodiments, the disease is Churg-Strauss syndrome or sinusitis.

Depending on the disease to be treated and the subject's condition, the compounds or compositions provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is the administration of the compounds provided herein in a depot formulation, in which the active ingredient is released over a predefined time period.

In the treatment, prevention, or amelioration of one or more symptoms of asthma, exercise induced asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with CRTH2 and/or one or more other $PGD_2$ receptors, an appropriate dosage level generally is about 0.001 to 100 mg per kg patient body weight per day (mg/kg per day), about 0.01 to about 75 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day. In certain embodiments, the dosage level is about 0.01 to about 75 mg/kg per day. In certain embodiments, the dosage level is about 0.1 to about 50 mg/kg per day. In certain embodiments, the dosage level is about 0.5 to about 25 mg/kg per day. In certain embodiments, the dosage level is about 1 to about 20 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Combination Therapy

Also provided is a method of modulating CRTH2 and/or one or more other PGD$_2$ receptors, comprising contacting the receptor(s) with one or more of the compounds or compositions provided herein. In one embodiment, the receptor(s) are expressed by a cell.

The compounds provided herein may also be combined or used in combination with other agents useful in the treatment, prevention, or amelioration of one or more symptoms of the diseases or conditions for which the compounds provided herein are useful, including asthma, exercise induced asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, and those pathologies noted above.

Other active agents to be used in combination with the compounds provided herein include, but are not limited to: inactivating antibodies (e.g., monoclonal or polyclonal) to interleukins (e.g., IL-4 and IL-5 (for example see Leckie et al. 2000 Lancet 356:2144)); soluble chemokine receptors (e.g. recombinant soluble IL-4 receptor (Steinke and Borish 2001 Respiratory Research 2:66)); chemokine receptor modulators including but not limited to antagonists of CCR1 (e.g., CP-481,715 (Gladue et al. J Biol Chem 278:40473)), CCR3 (e.g., UCB35625 (Sabroe et al. J Biol Chem 2000 275:25985) and CCR5; histamine H1 receptor antagonists/antihistamines (i.e. any compound that is capable of blocking, inhibiting, reducing or otherwise interrupting the interaction between histamine and its receptor) including but not limited to: asternizole, acrivastine, antazoline, asternizole, azatadine, azelastine, bromopheniramine, carbinoxamine, carebastine, cetirizine, chlorpheniramine, clemastine, cyclizine, cyproheptadine, descarboethoxyloratadine, dexchlorpheniramine, dimethindene, diphenhydramine, diphenylpyraline, doxylamine, ebastine, efletirizine, epinastine, fexofenadine, hydroxyzine, hydroxyzine, ketotifen, levocabastine, levocetirizine, levocetirizine, loratadine, meclizine, mequitazine, methdilazine, mianserin, mizolastine, noberastine, norasternizole, noraztemizole, pheniramine, picumast, promethazine, pyrilamine, temelastine, terfenadine, trimeprazine, tripelenamine, and triprolidin; leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafirlukast, montelukast, montelukast sodium (Singulair®), pranlukast, iralukast and pobilukast; PGD2 receptor antagonists including, but not limited to, compounds having PGD2 antagonizing activity; VLA-4 antagonists; corticosteroids, such as beclomethasone, methylprednisolone, betamethasone, prednisone, prenisolone, triamcinolone, dexamethasone, fluticasone, flunisolide and hydrocortisone, and corticosteroid analogs such as budesonide; immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®); non-steroidal anti-asthmatics such as .beta.2-agonists (e.g., terbutaline, metaproterenol, fenoterol, isoetharine, albuterol, salmeterol, bitolterol and pirbuterol) and .beta.2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005); non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); cyclooxygenase-2 (COX-2) inhibitors such as celecoxib (Celebrex®), rofecoxib (Vioxx®), valdecoxib, etoricoxib, parecoxib and lumiracoxib; inhibitors of phosphodiesterase type IV (PDE-I); opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; antithrombotic agents, such as thrombolytic agents (e.g., streptokinase, alteplase, anistreplase and reteplase), heparin, hirudin and warfarin derivatives, .beta.-blockers (e.g., atenolol), .beta.-adrenergic agonists (e.g., isoproterenol), ACE inhibitors and vasodilators (e.g., sodium nitroprusside, nicardipine hydrochloride, nitroglycerin and enaloprilat); anti-diabetic agents such as insulin and insulin mimetics, insulin derivatives such as, for example, Lantus®, sulfonylureas (e.g., glyburide, meglinatide, tolbutamide, glibenclamide, glipizide or glimepiride), biguanides, e.g., metformin (Glucophage®), meglitinides (for example, repaglinide), oxadiazolidinediones, glucosidase inhibitors (for example, miglitol or acarbose), insulin sensitizers, including but not limited to thiazolidinone compounds (for example, rosiglitazone (Avandia®), troglitazone (Rezulin®), ciglitazone, pioglitazone (Actos®) and englitazone); glucagon antagonists; GLP-1 agonists; exendin-4; exenatine; potassium channel openers; HMGCoA reductase inhibitors (for example, simvastatin, fluvastatin, pravastatin, lovastatin, atorvastatin and cerivastatin); cholesterol absorption inhibitors (for example, ezetimibe, tiqueside and pamaqueside); fibrates such as, for example, fenofibrate, clofibrate and bezafibrate; rosuvastatin preparations of interferon beta (interferon .beta.-I.alpha., interferon .beta.-I.beta.); gold compounds such as auranofin and aurothioglucose; TNF inhibitors, e.g., etanercept (Enbrel®), antibody therapies such as orthoclone (OKT3), daclizumab (Zenapax®), basiliximab (Simulec®)), infliximab (Remicade®) and D2E6 TNF antibody; lubricants or emollients such as petrolatum and lanolin, keratolytic agents, vitamin D.sub.3 derivatives (e.g., calcipotriene and calcipotriol (Dovonex®)), PUVA, anthralin (Drithrocreme®), etretinate (Tegison®) and isotretinoin; multiple sclerosis therapeutic agents such as interferon .beta.-I.beta. (Betaseron®), interferon .beta.-I.alpha. (Avonex®), azathioprine (Imurek®, Imuran®), glatiramer acetate (Capoxone®), a glucocorticoid (e.g., prednisolone) and cyclophosphamide; and other compounds such as 5-aminosalicylic acid and prodrugs thereof DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (ST1571, Gleevec®) and rituximab (Rituxan®).

In another embodiment, the compounds provided herein can be administered in combination with an MTP inhibitor such as, for example, implitapide, BMS-201038, R-103757. In another embodiment, the compounds provided herein can be administered in combination with bile acid absorption inhibitor (see, for example, U.S. Pat. No. 6,245,744 or U.S. Pat. No. 6,221,897), such as, for example, HMR 1741; a CETP inhibitor, such as, for example, JTF-705; a polymeric bile acid adsorbent such as, for example, cholestyramine, colesevelam; an LDL receptor inducer (see U.S. Pat. No. 6,342,512), such as, for example, HMR1171, HMR1586; an ACAT inhibitor, such as, for example, avasimibe; an antioxidant, such as, for example, OPC-14117; a lipoprotein lipase inhibitor, such as, for example, NO-1886; an ATP-citrate lyase inhibitor, such as, for example, SB-204990; a squalene synthetase inhibitor, such as, for example, BMS-188494; a lipoprotein(a) antagonist, such as, for example, CI-1027; nicotinic acid; a lipase inhibitor, such as, for example, orlistat (Xenical®, Alli); immunosuppressant drugs, such as, cyclosporin A, substituted xanthines (e.g. methylxanthines such as pentoxyfylline), tacrolimus, rapamycin (and derivatives thereof), leflunomide (or its main active metabolite A771726, or analogs thereof called malononitrilamides), mycophenolic acid and salts thereof (including the sodium salt marketed under the trade name Mofetil®), adrenocortical steroids (for example, dexamethasone, methylprednisolone, methotrexate, prednisone, prednisolone, triamcinolone and pharmaceutically acceptable salts thereof), azathioprine, brequinar, gusperimus, 6-mercaptopurine, mizoribine, chloroquine, hydroxychloroquine and monoclonal antibodies with immunosuppressive properties; immunomodulators, such as, acemannan, amiprilose, bucillamine, ditiocarb sodium, imiquimod, inosine pranobex(Isoprinosine®, Immunovir®, Delimmun®), interferon-.beta., interferon-.gamma., lentinan, levamisole, pidotimod, romurtide, platonin, procodazole, propagermanium, thymomodulin, thymopentin and ubenimex.

In another embodiment, the compounds provided herein can be administered in combination with an agent used to treat asthma or exercise induced asthma, including, but not limited to: albuterol (Accuneb®, ProAir HFA®, Proventil®, Ventolin®, Vospire®), beclomethasone (Qvar®), budesonide (Pulmicort®), cromolyn (Intal®), terbutaline (Brethine®), metaproterenol (Alupent®), theophylline (Quibron-T®, Elixophyllin®, Uniphyl®), theophylline ethylenediamine (Aminophylline®), ephedrine, epinephrine, flunisolide (Aerobid®), fluticasone (Flovent®), levabuterol (Xopenex®), mometazone (Asmanex®), montelukast sodium (Singulair®), nedocromil (Tilade®), triamcinolone (Azmacort®), fenoterol, isoetharine, salmeterol, bitolterol, dyphylline (Dilor®, Dylix®, Lufyllin®), dyphylline/guaifenesin (COPD®, Lufyllin-GG®, Ed-Bron G®), Primatene Asthma®, pirbuterol (Maxair®), zafirlukast (Accolate®) or zileuton (Zyflo®).

In another embodiment, the compounds provided herein can be administered in combination with an agent used to treat multiple sclerosis, including, but not limited to: betamethasone (Celestone®), hydrocortisone (A-Hydrocort®, Cortef®), hydrocortisone sodium succinate (Solu-Cortef®), corticotropin (Acthar®), methylprednisolone (A-Methapred®, Medrol®, Depo-Medrol®, Meprolone®), methylprednisolone sodium succinate (Solu-Medrol®), dexamethasone (DexPak®, Dexacort®), triamcinolone (Kenalog®), triamcinolone acetonide, prednisolone (Prelone®, Orapred®, Sterapred®, Pediapred®), interferon beta-1a (Avonex®, Rebif®), interferon beta-1b (Betaseron®), baclofen (Kemstro®, Lioresal®), glatiramer (Copaxone®), dantrolene sodium (Dantrium®), mitoxantrone, mitoxantrone hydrochloride (Novantrone®), natalizumab (Tysabri®), tizanidine (Zanaflex®, Sirdalud®), amantadine, *clostridium botulinum* toxin (Botox®), cyclophosphamide (Neosar®, Cytoxan®) or cycloheptadine.

In another embodiment, the compounds provided herein can be administered in combination with an agent used to treat inflammatory bowel disease, including, but not limited to: adalimumab (Humria®), loperamide (Diamode®, Immodium®, Kaopectate 1-D®, Maalox®, Imperim®, Pepto Diarrhea Control®), azathioprine (Imuran®), betamethasone (Celestone®), hydrocortisone (A-Hydrocort®, Cortef®), corticotropin (Acthar®), methylprednisolone (A-Methapred®, Medrol®, Depo-Medrol®, Meprolone®), dexamethasone (DexPak®, Dexacort®), osalazine (Dipentum®), cromolyn (Gastrocrom®), triamcinolone (Kenalog®, Aristocort®, Triacet®), mercaptopurine (Purinethol®) or prednisolone (Prelone®, Orapred®, Sterapred®, Pediapred®).

In another embodiment, the compounds provided herein can be administered in combination with an agent used to treat transplant rejection, including, but not limited to: betamethasone (Celestone®), hydrocortisone (A-Hydrocort®, Cortef®), corticotropin (Acthar®), methylprednisolone (A-Methapred®, Medrol®, Depo-Medrol®, Meprolone®), dexamethasone (DexPak®, Dexacort®), triamcinolone (Kenalog®, Aristocort®, Triacet®), cyclosporine (Neoral®, Sandimmune®, Gengraf®), muromonab (Orthoclone OKT3®), tacrolimus (Prograf®) or prednisolone (Prelone®, Orapred®, Sterapred®, Pediapred®).

Such other agents, or drugs, may be administered, by a route and in an amount commonly used therefor, simultaneously or sequentially with a compound or composition provided herein. When a compound provided herein is used contemporaneously with one or more other drugs, a pharmaceutical composition containing such other drugs in addition to the compound provided herein may be utilized, but is not required. Accordingly, the pharmaceutical compositions provided herein include those that also contain one or more other active ingredients or therapeutic agents, in addition to a compound provided herein.

The weight ratio of the compound provided herein to the second active ingredient may be varied, and will depend upon the effective dose of each ingredient. Generally, an effective dose of each will be used. Thus, for example, when a compound provided herein is combined with a NSAID, the weight ratio of the compound provided herein to the NSAID may range from about 1,000:1 to about 1:1,000, or about 200:1 to about 1:200. Combinations of a compound provided herein and other active ingredients will generally also be within the aforementioned range, but in each case, an effective dose of each active ingredient should be used.

EXAMPLES

Synthesis of 2-(4-chloro-6-(dimethylamino)-2-(4-(4-(trifluoromethyl)-benzamido)benzylthio)pyrimidin-5-yl)acetic acid (5) and 2-(4-chloro-6-(dimethylamino)-2-(4-(4-fluorobenzamido)benzylthio)pyrimidin-5-yl)acetic acid (6)

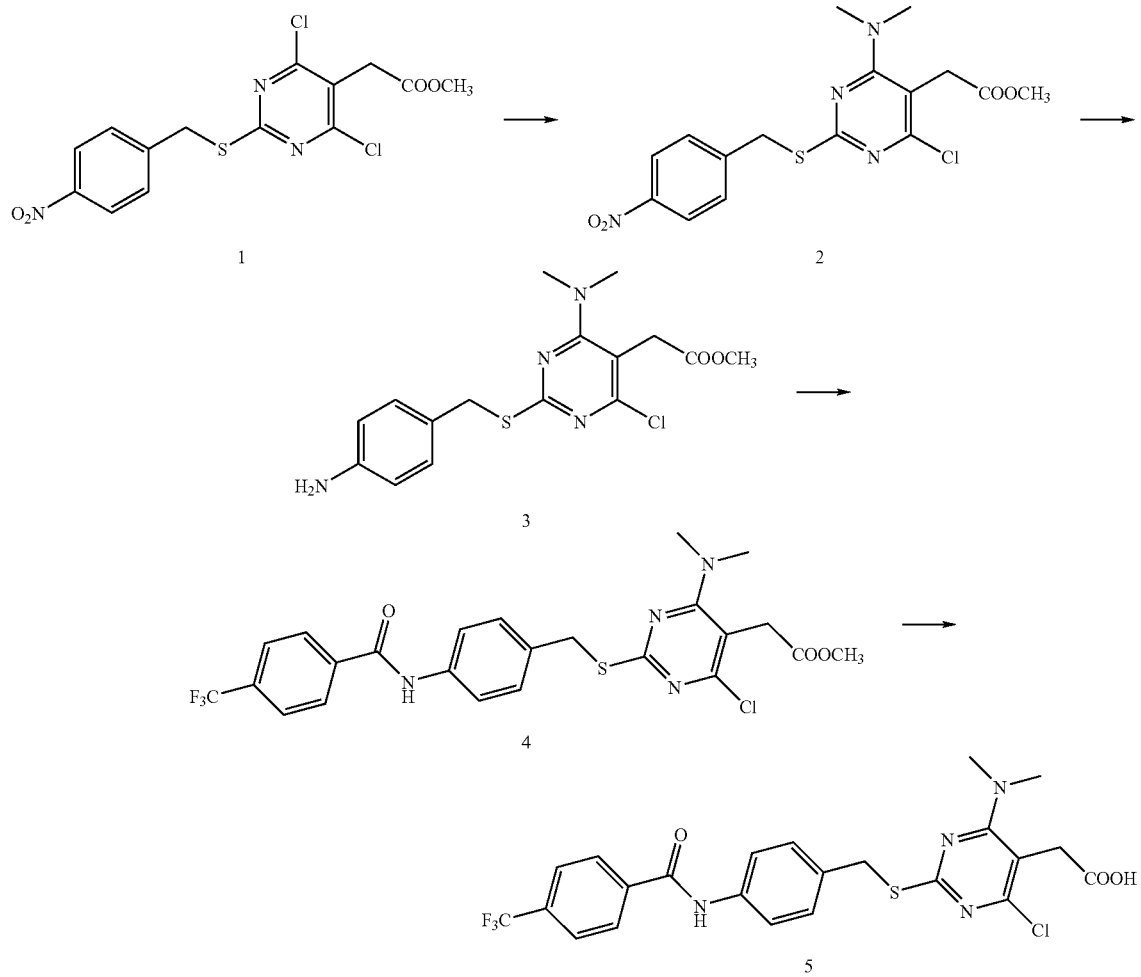

Methyl 2-(4,6-dichloro-2-(4-nitrobenzylthio)pyrimidin-5-yl)acetate (1) was prepared by methods known in the art, for example, the process described in GB 2,359,078.

Preparation of methyl 2-(4-chloro-6-(dimethylamino)-2-(4-nitrobenzylthio)-pyrimidin-5-yl)acetate (2). To a solution of 1 (0.37 g) in tetrahydrofuran (5.00 mL) at room temperature was added potassium carbonate (0.66 g) and dimethylamine hydrochloride (0.09 g). The resulting suspension was stirred at room temperature for 16 hours and filtered. The remaining residue was rinsed with ethyl acetate and the filtrate was washed sequentially with 1N HCl, water, and brine, dried over anhydrous magnesium sulfate, filtered, and concentrated in vacuo. The crude product thus obtained as a dark oil was purified by flash chromatography over silica gel eluting with 25% ethyl acetate in hexanes to give pure compound 2 as a white powder (0.20 g).

Preparation of methyl 2-(2-(4-aminobenzylthio)-4-chloro-6-(dimethylamino)-pyrimidin-5-yl)acetate (3). To a suspension of 2 (1.11 g) in ethanol (25 mL0 at room temperature was added tin(II) chloride dehydrate (3.81 g) and the resulting mixture was refluxed for 2 hours. After cooling to rt, the volume was reduce by approximately half by concentration in vacuo and the remaining clear yellow solution was poured into chilled saturated sodium bicarbonate solution. The resulting white suspension was treated with EtOAc and filtered through Celite. The filtrate was allowed to separate and the aqueous layer was extracted with EtOAc thrice. The combined organic extracts was washed with water and brine, dried over anhydrous MgSO4, filtered, and concentrated in vacuo to give crude 3 as an orange oil (1.12 g).

Preparation of 2-(4-chloro-6-(dimethylamino)-2-(4-(4-(trifluoromethyl)benzamido)benzylthio)pyrimidin-5-yl)acetic acid (5). To a solution of 3 (0.10 g) and triethylamine (0.12 mL) in dichloromethane (2 mL) chilled in an ice-bath was added 4-trifluoromethylbenzoyl chloride (0.05 mL). The ice-bath was removed and the reaction mixture was allowed to warm to room temperature. After stirring at room temperature for 1 hour, the reaction mixture was partitioned between dichloromethane and 1N HCl solution. The separated organic layer was washed with water and brine, dried over anhydrous magnesium sulfate, filtered, and concentrated in vacuo. The crude product thus obtained as a white powder was triturated with diisopropylether and filtered to give compound 4 as a white powder (0.16 g) which was dissolved in tetrahydrofuran (4.00 mL) and treated with 1N NaOH solution (1.00 mL). Methanol was introduced dropwise until a homogeneous reaction mixture was achieved. After stirring at room temperature for 16 hours, the volatiles were removed in vacuo and the remaining white suspension was diluted with some water, treated with diethylether, stirred vigorously for 1 minute, and allowed to separate. The separated organic layer was decanted and the remaining aqueous suspension was chilled in an ice-bath and carefully acidified to pH~4. The separated solids were collected by suction and rinsed with water and dried to furnish compound 5 as a white powder (0.11 g).

Preparation of 2-(4-chloro-6-(dimethylamino)-2-(4-(4-fluorobenzamido)benzylthio)pyrimidin-5-yl)acetic acid (6)

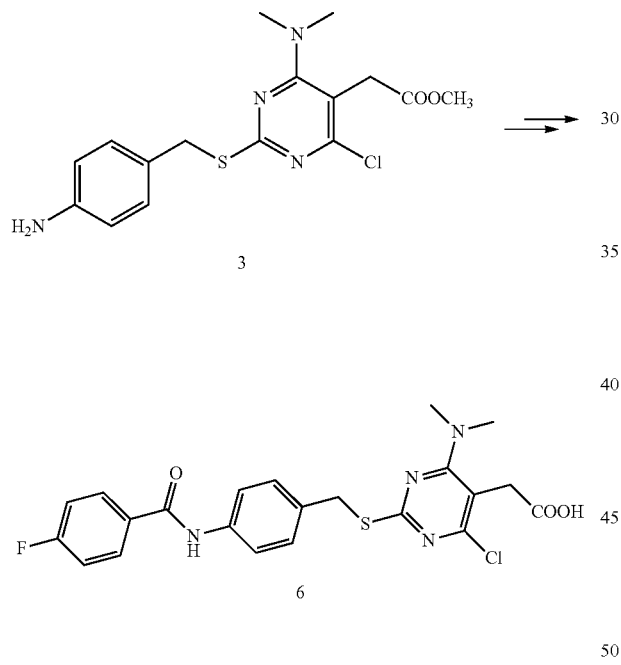

A solution of 3 (0.10 g) in dichloromethane (2.00 mL) at room temperature was treated with 4-fluorobenzoic acid (0.06 g), triethylamine (0.07 mL), and 4-dimethylaminopyridine (0.04 g). When all solids have dissolved, 1-(3-dimethylaminopropyl)-3-ethylcarbodiimide hydrochloride (0.11 g) was added. After stirring at room temperature for 16 hours, the reaction mixture was partitioned between dichloromethane and 1N HCl solution, the separated organic layer was collected and washed sequentially with water and brine, dried over anhydrous magnesium sulfate, filtered, and concentrated in vacuo to give a light green oil from which the crude methyl ester intermediate (0.09 g) was obtained as a white powder by trituration with dichloromethane and diisopropylether. Hydrolysis of the intermediate using the same procedure as detailed above gave compound 6 as a white powder (0.07 g).

What is claimed is:
1. A compound having formula I:

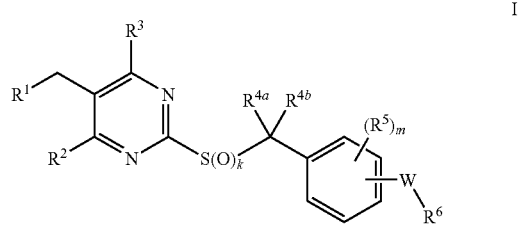

or a pharmaceutically acceptable salt, stereoisomer or tautomer thereof, wherein $R^1$ is —$CO_2H$, —$C(O)NR^{8a}R^{8b}$, nitrile or tetrazolyl;
$R^{4a}$ and $R^{4b}$ are each independently hydrogen or ($C_1$-$C_6$) alkyl;
in each instance, independently, W, $R^2$, $R^3$, $R^5$, $R^6$, $R^{8a}$, $R^{8b}$, k and m are selected from (I) or (II) as follows:
(I) W is a single bond, —$(CH_2)_m$—, —O—, —S(O)$_n$—, —$NR^7$—, —C(O)—, —C(O)O—, —$C(O)NR^7$—, —$NR^7C(O)NR^7$— or —$NR^7C(O)$O—;
  in each instance, independently, $R^2$ and $R^3$ are selected from (i) or (ii) as follows:
  (i) $R^2$ and $R^3$ are each independently (a) hydrogen; (b) F; (c) Br; (d) I; (e) ($C_1$-$C_6$)alkyl; (f) ($C_1$-$C_6$)alkyl substituted by aryl, hydroxy, carboxy, alkoxy, carbamoyl, ($C_1$-$C_6$)alkylcarbamoyl, di($C_1$-$C_6$)alkyl)carbamoyl, ($C_3$-$C_7$)cycloalkylcarbamoyl or ($C_3$-$C_7$) heterocyclylcarbamoyl; (g) ($C_1$-$C_6$)alkyl substituted by mono-, di-, or tri-halogen; (h) ($C_3$-$C_7$)cycloalkyl; (i) —$SR^9$; (j) —$NR^{10}R^{11}$; or (k) ($C_1$-$C_6$)alkoxy optionally substituted by mono-, di-, or tri-halogen; or
  (ii) $R^2$ and $R^3$ are each independently (a) hydrogen; (b) Cl; (c) ($C_1$-$C_6$)alkyl; (d) ($C_1$-$C_6$)alkyl substituted by aryl, hydroxy, carboxy, alkoxy, carbamoyl, ($C_1$-$C_6$)alkylcarbamoyl, di($C_1$-$C_6$) alkyl)carbamoyl, ($C_3$-$C_7$)cycloalkylcarbamoyl or ($C_3$-$C_7$)heterocyclylcarbamoyl; (e) ($C_1$-$C_6$) alkyl substituted by mono-, di-, or tri-halogen; (f) ($C_3$-$C_7$)cycloalkyl; (g) —$SR^9$; (h) —$NR^{12}R^{13}$; or (i) ($C_1$-$C_6$)alkoxy optionally substituted by mono-, di-, or tri-halogen;
  each $R^5$ is independently (a) hydrogen; (b) halogen; (c) cyano; (d) nitro; (e) hydroxy; (f) phenyl; (g) phenyloxy; (h) benzyl; (i) benzyloxy; (j) guanidino; (k) heterocyclyl; (l) —$NR^{14}R^{15}$; (m) sulfamoyl; (n) ($C_1$-$C_6$)alkylsulfonyl; (o) ($C_1$-$C_6$) alkylaminosulfonyl; (p) di($C_1$-$C_6$)alkylaminosulfonyl; (q) —$C(O)R^9$; (r) —$C(O)OR^9$; (s) —$C(O)NR^{8a}R^{8b}$; (t) —$NR^7C(O)R^9$; (u) —OC(O)$NR^{8a}R^{8b}$; (v) —$NR^7C(O)OR^9$; (w) ($C_2$-$C_6$) alkenyl; (x) ($C_1$-$C_6$)alkyl optionally substituted by mono-, di-, or tri-halogen; (y) ($C_1$-$C_6$)alkoxy optionally substituted by mono-, di-, or tri-halogen; or (z) ($C_1$-$C_6$)alkylthio optionally substituted by mono-, di-, or tri-halogen;
  $R^6$ is (a) hydrogen; (b) ($C_1$-$C_6$)alkyl; (c) ($C_2$-$C_6$) alkenyl; (d) ($C_2$-$C_6$)alkynyl; (e) ($C_3$-$C_7$)cycloalkyl; (f) ($C_1$-$C_6$)alkyl substituted by aryl or heteroaryl; (g) ($C_2$-$C_4$)alkenyl substituted by aryl or heteroaryl; (h) $(C_1-C_6)$alkyl substituted by mono-, di-, or tri-halogen; (i) $(C_1-C_6)$alkyl substituted by —C(O)R$^{6a}$; (j) $(C_1-C_6)$alkoxy substituted by mono-, di-, or tri-halogen; (k) $(C_1-C_6)$alkylthio substituted by mono-, di-, or tri-halogen; (l) aryl; or (m) heteroaryl; wherein said aryl and heteroaryl are optionally substituted with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —NR$^{8a}$R$^{8b}$; (l) —C(O)R$^9$; (m) —C(O)NR$^{8a}$R$^{8b}$; (n) —OC(O)NR$^{8a}$R$^{8b}$; (o) —C(O)OR$^9$; (p) —NR$^7$C(O)OR$^9$; (q) —NR$^7$C(O)R$^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

R$^{6a}$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkyl substituted by mono-, di-, or tri-halogen; (i) $(C_1-C_6)$alkoxy substituted by mono-, di-, or tri-halogen; (j) $(C_1-C_6)$alkylthio substituted by mono-, di-, or tri-halogen; (k) aryl; or (l) heteroaryl; wherein said aryl and heteroaryl are optionally substituted with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) —NR$^{8a}$R$^{8b}$; (l) —C(O)R$^9$; (m) —C(O)NR$^{8a}$R$^{8b}$; (n) —OC(O)NR$^{8a}$R$^{8b}$; (o) —C(O)OR$^9$; (p) —NR$^7$C(O)OR$^9$; (q) —NR$^7$C(O)R$^9$; (r) sulfamoyl; (s) $(C_1-C_6)$alkylsulfonyl; (t) $(C_1-C_6)$alkylaminosulfonyl; (u) di$(C_1-C_6)$alkylaminosulfonyl; (v) $(C_1-C_6)$alkyl optionally substituted by mono-, di-, or tri-halogen; (w) $(C_1-C_6)$alkoxy optionally substituted by mono-, di-, or tri-halogen; and (x) $(C_1-C_6)$alkylthio optionally substituted by mono-, di-, or tri-halogen;

each R$^7$ is independently (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl;

in each instance, independently, R$^{8a}$ and R$^{8b}$ are selected from (i) or (ii) as follows:
(i) R$^{8a}$ and R$^{8b}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
(ii) each R$^{8a}$ and R$^{8b}$, together with the N to which they are bonded, independently may form a 3 to 8 membered saturated or unsaturated ring optionally containing one or more O or S atoms, or one or more additional N atoms, in the ring;

each R$^9$ is independently (a) hydrogen; (b) $(C_1-C_6)$alkyl; phenyl; or (c) $(C_1-C_6)$alkyl substituted by aryl, alkoxy or mono-, di-, or tri-halogen;

in each instance, independently, R$^{10}$ and R$^{11}$ are selected from (i) or (ii) as follows:
(i) R$^{10}$ and R$^{11}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
(ii) each R$^{10}$ and R$^{11}$, together with the N to which they are bonded, independently may form a 3 to 8 membered saturated or unsaturated ring optionally containing one or more O or S atoms, or one or more additional N atoms, in the ring;

in each instance, independently, R$^{12}$ and R$^{13}$ are selected from (i), (ii), (iii) or (iv) as follows:
(i) R$^{12}$ and R$^{13}$ are each independently selected from (a) hydrogen; (b) $(C_1-C_6)$alkyl; (c) phenyl; (d) $(C_1-C_6)$alkyl substituted by aryl, hydroxy, carboxy or alkoxy; (e) $(C_1-C_6)$alkyl substituted by mono-, di-, or tri-halogen; or (f) $(C_3-C_7)$cycloalkyl;
(ii) R$^{12}$ and R$^{13}$, together with the N to which they are bonded, form a 5 membered saturated ring containing at least one O or S atom, or at least one additional N atom, in the ring;
(iii) R$^{12}$ and R$^{13}$, together with the N to which they are bonded, form a 5 membered unsaturated ring, optionally containing one or more O or S atom, or one or more additional N atoms, in the ring; or
(iv) R$^{12}$ and R$^{13}$, together with the N to which they are bonded, form a 3, 4, 6, 7 or 8 membered saturated or unsaturated ring, optionally containing one or more O or S atoms, or one or more additional N atoms, in the ring;

in each instance, independently, R$^{14}$ and R$^{15}$ are selected from (i) or (ii) as follows:
(i) R$^{14}$ and R$^{15}$ are each independently selected from (a) hydrogen; (b) $(C_1-C_6)$alkyl; (c) phenyl; (d) $(C_1-C_6)$alkyl substituted by aryl, hydroxy, carboxy, alkoxy, carbamoyl, $(C_1-C_6)$alkylcarbamoyl, di$((C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; or (f) $(C_3-C_7)$cycloalkyl; or
(ii) each R$^{14}$ and R$^{15}$, together with the N to which they are bonded, independently may form a 3 to 8 membered saturated or unsaturated ring optionally containing one or more O or S atoms, or one or more additional N atoms, in the ring;

k is 0, 1 or 2;
each m is independently 1, 2, 3 or 4; and
n is 0, 1 or 2; or (II) one of R$^5$ groups and W—R$^6$ together with the atoms to which they are attached may form a 4 to 8 membered unsaturated ring optionally containing one or more N, O or S atoms in the ring, wherein the ring is optionally substituted with one or more R$^{5a}$ groups;

$R^2$ and $R^3$ are each independently (a) hydrogen; (b) F; (c) Cl; (d) Br; (e) I; (f) ($C_1$-$C_6$)alkyl; (g) ($C_1$-$C_6$)alkyl substituted by aryl, hydroxy, carboxy, alkoxy, carbamoyl, ($C_1$-$C_6$)alkylcarbamoyl, di($C_1$-$C_6$)alkyl)carbamoyl, ($C_3$-$C_7$)cycloalkylcarbamoyl or ($C_3$-$C_7$)heterocyclylcarbamoyl; (h) ($C_1$-$C_6$)alkyl substituted by mono-, di-, or tri-halogen; (i) ($C_3$-$C_7$)cycloalkyl; (j) —$SR^9$; (k) —$NR^{10}R^{11}$; or (l) ($C_1$-$C_6$)alkoxy optionally substituted by mono-, di-, or tri-halogen;

the remaining $R^5$ groups and $R^{5a}$ are each independently (a) hydrogen; (b) halogen; (c) cyano; (d) nitro; (e) hydroxy; (f) phenyl; (g) phenyloxy; (h) benzyl; (i) benzyloxy; (j) guanidino; (k) heterocyclyl; (l) —$NR^{14}R^{15}$; (m) sulfamoyl; (n) ($C_1$-$C_6$)alkylsulfonyl; (o) ($C_1$-$C_6$)alkylaminosulfonyl; (p) di($C_1$-$C_6$)alkylaminosulfonyl; (q) —$C(O)R^9$; (r) —$C(O)OR^9$; (s) —$C(O)NR^{8a}R^{8b}$; (t) —$NR^7C(O)R^9$; (u) —$OC(O)NR^{8a}R^{8b}$; (v) —$NR^7C(O)OR^9$; (w) ($C_2$-$C_6$)alkenyl; (x) ($C_1$-$C_6$)alkyl optionally substituted by mono-, di-, or tri-halogen; (y) ($C_1$-$C_6$)alkoxy optionally substituted by mono-, di-, or tri-halogen; or (z) ($C_1$-$C_6$)alkylthio optionally substituted by mono-, di-, or tri-halogen;

each $R^7$ is independently (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl;

in each instance, independently, $R^{8a}$ and $R^{8b}$ are selected from (i) or (ii) as follows:
(i) $R^{8a}$ and $R^{8b}$ are each independently selected from (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; or
(ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

each $R^9$ is independently (a) hydrogen; (b) ($C_1$-$C_6$)alkyl; phenyl; or (c) ($C_1$-$C_6$)alkyl substituted by aryl, alkoxy or mono-, di-, or tri-halogen;

in each instance, independently, $R^{10}$ and $R^{11}$ are selected from (i) or (ii) as follows:
(i) $R^{10}$ and $R^{11}$ are each independently selected from (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring;

in each instance, independently, $R^{14}$ and $R^{15}$ are selected from (i) or (ii) as follows:
(i) $R^{14}$ and $R^{15}$ are each independently selected from (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; or
(ii) each $R^{14}$ and $R^{15}$, together with the N to which they are bonded, independently may form a 3 to 8 membered saturated or unsaturated ring optionally containing one or more O or S atoms, or one or more additional N atoms, in the ring;

k is 0, 1 or 2; and m is 1, 2, 3 or 4.

2. The compound of claim 1 wherein, in each instance, independently, $R^{10}$ and $R^{11}$ are selected from (i) or (ii) as follows:
(i) $R^{10}$ and $R^{11}$ are each independently selected from (a) hydrogen; (b) ($C_1$-$C_6$)alkyl; (c) phenyl; (d) ($C_1$-$C_6$)alkyl substituted by unsubstituted phenyl, hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and in each instance, independently, $R^{12}$ and $R^{13}$ are selected from (i), (ii), (iii) or (iv) as follows:
(i) $R^{12}$ and $R^{13}$ are each independently selected from (a) hydrogen; (b) ($C_1$-$C_6$)alkyl; (c) phenyl; (d) ($C_1$-$C_6$)alkyl substituted by unsubstituted phenyl, hydroxy, carboxy or alkoxy; (e) ($C_1$-$C_6$)alkyl substituted by mono-, di-, or tri-halogen; or (f) ($C_3$-$C_7$)cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more 0 or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

3. The compound of claim 1 wherein, in each instance, independently, $R^{10}$ and $R^{11}$ are selected from (i) or (ii) as follows:
(i) $R^{10}$ and $R^{11}$ are each independently selected from (a) hydrogen; (b) ($C_1$-$C_6$)alkyl; (c) phenyl; (d) ($C_1$-$C_6$)alkyl substituted by hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and in each instance, independently, $R^{12}$ and $R^{13}$ are selected from (i), (ii), (iii) or (iv) as follows:
(i) $R^{12}$ and $R^{13}$ are each independently selected from (a) hydrogen; (b) $(C_1-C_6)$alkyl; (c) phenyl; (d) $(C_1-C_6)$alkyl substituted by hydroxy, carboxy or alkoxy; (e) $(C_1-C_6)$ alkyl substituted by mono-, di-, or tri-halogen; or (f) $(C_3-C_7)$cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more 0 or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

4. The compound of claim 1 wherein, in each instance, independently, $R^{10}$ and $R^{11}$ are selected from (i) or (ii) as follows:
(i) $R^{10}$ and $R^{11}$ are each independently selected from (a) hydrogen; (b) $(C_1-C_6)$alkyl; (c) phenyl; (d) $(C_1-C_6)$alkyl substituted by mono-, di-, or tri-halogen; or (e) $(C_3-C_7)$ cycloalkyl; or
(ii) each $R^{10}$ and $R^{11}$, together with the N to which they are bonded, independently may form a 3 to 8 membered saturated or unsaturated ring optionally containing one or more O or S atoms, or one or more additional N atoms, in the ring; and
in each instance, independently, $R^{12}$ and $R^{13}$ are selected from (i), (ii), (iii) or (iv) as follows:
(i) $R^{12}$ and $R^{13}$ are each independently selected from (a) hydrogen; (b) $(C_1-C_6)$alkyl; (c) phenyl; (d) $(C_1-C_6)$alkyl substituted by mono-, di-, or tri-halogen; or (e) $(C_3-C_7)$ cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more 0 or S atom, or one or more additional N atoms, in the ring; or
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring.

5. The compound of claim 1 wherein $R^1$ is $-CO_2H$.

6. The compound of claim 1 wherein $R^{4a}$ and $R^{4b}$ are each independently hydrogen.

7. A compound having formu II:

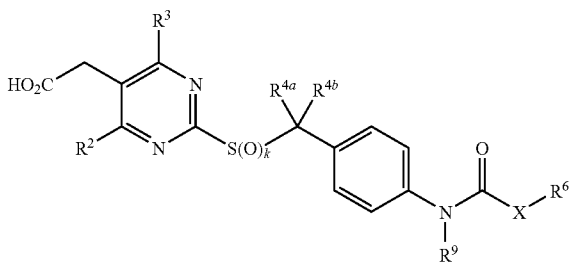

II or a pharmaceutically acceptable salt, stereoisomer or tautomer thereof, wherein
X is a single bond, $-O(CH_2)_p-$ or $-NR^9(CH_2)_p-$;
in each instance, independently, $R^2$ and $R^3$ are selected from (i) and (ii) as follows:
(i) $R^2$ and $R^3$ are each independently (a) hydrogen; (b) F; (c) Br; (d) (e) $(C_1-C_6)$alkyl; (f) $(C_1-C_6)$alkyl substituted by aryl, hydroxy, carboxy, alkoxy, carbamoyl, $(C_1-C_6)$alkylcarbamoyl, di$(C_1-C_6)$alkyl) carbamoyl, $(C_3-C_7)$cycloalkylcarbamoyl or $(C_3-C_7)$heterocyclylcarbamoyl; (g) $(C_1-C_6)$alkyl substituted by mono-, di-, tri-halogen; (h) $(C_3-C_7)$ cycloalkyl; (i) $-SR^9$; (j) $-NR_{10}R^{11}$; or (k) $(C_1-C_6)$alkoxy optionally substituted by mono-, di-, or tri-halogen; and
(ii) $R^2$ and $R^3$ are each independently (a) hydrogen; (b) Cl; (c) $(C_1-C_6)$alkyl; (d) $(C_1-C_6)$alkyl substituted by aryl, hydroxy, carboxy, alkoxy, carbamoyl, $(C_1-C_6)$alkylcarbamoyl, di$(C_1-C_6)$alkyl)carbamoyl, $(C_3-C_7)$cycloalkylcarbamoyl or $(C_3-C_7)$heterocyclylcarbamoyl; (e) $(C_1-C_6)$alkyl substituted by mono-, di-, or tri-halogen; (f) $(C_3-C_7)$cycloalkyl; (g) $-SR^9$; (h) $-NR^{12}R^{13}$; or (i) $(C_1-C_6)$ alkoxy optionally substituted by mono-, di-, or tri-halogen;
$R^{4a}$ and $R^{4b}$ are each independently hydrogen or $(C_1-C_6)$ alkyl;
$R^6$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$ alkenyl substituted by aryl or heteroaryl; (h) $(C_1-C_6)$ alkyl substituted by mono-, di-, or tri-halogen; (i) $(C_1-C_6)$alkyl substituted by $-C(O)R^{6a}$; (j) $(C_1-C_6)$ alkoxy substituted by mono-, di- or tri-halogen; (k) $(C_1-C_6)$alkylthio substituted by mono-, di-, or tri-halogen; (l) aryl; or (m) heteroaryl; wherein said aryl and heteroaryl are optionally substituted with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k)-$NR^{8a}R^{8b}$; (l) $-C(O)R^9$; (m) $-C(O)NR^{8a}R^{8b}$; (n) $-OC(O)$ $NR^{8a}R^{8b}$; (o) $-C(O)OR^9$; (p) $-NR^7C(O)OR^9$; (q) $-NR^7C(O)R^9$; (r) sulfamoyl; (s) $(C_1-C_6)$alkylsulfonyl; (t) $(C_1-C_6)$alkylaminosulfonyl; (u) di$(C_1-C_6)$ alkylaminosulfonyl; (v) $(C_1-C_6)$alkyl optionally substituted by mono-, di-, or tri-halogen; (w) $(C_1-C_6)$ alkoxy optionally substituted by mono-, di-, or tri-halogen; and (x) $(C_1-C_6)$alkylthio optionally substituted by mono-, di-, or tri-halogen;
$R^{6a}$ is (a) hydrogen; (b) $(C_1-C_6)$alkyl; (c) $(C_2-C_6)$alkenyl; (d) $(C_2-C_6)$alkynyl; (e) $(C_3-C_7)$cycloalkyl; (f) $(C_1-C_6)$alkyl substituted by aryl or heteroaryl; (g) $(C_2-C_4)$alkenyl substituted by aryl or heteroaryl; (h) $(C_1-C_6)$alkynyl; substituted by mono-, di-, or tri-halogen; (i) $(C_1-C_6)$alkoxy substituted by mono-, di-, or tri-halogen; (j) $(C_1-C_6)$alkylthio substituted by mono-, di-, or tri-halogen; (k) aryl; or (l) heteroaryl; wherein said aryl and heteroaryl are optionally substituted with one or more substituents selected from the group consisting of (a) halogen; (b) cyano; (c) nitro; (d) hydroxy; (e) guanidino; (f) heterocyclyl; (g) phenyl; (h) phenyloxy; (i) benzyl; (j) benzyloxy; (k) $-NR^{8a}R^{8b}$; (l) $-C(O)R^9$; (m) $-C(O)NR^{8a}R^{8b}$; (n) $-OC(O)NR^{8a}R^{8b}$; (o) $-C(O)OR^9$; (p) $-NR^7C(O)$ $OR^9$; (q) $-NR^7C(O)R^9$; (r) sulfamoyl; (s) $(C_1-C_6)$ alkylsulfonyl; (t) $(C_1-C_6)$alkylaminosulfonyl; (u)

di($C_1$-$C_6$)alkylaminosulfonyl; (v) ($C_1$-$C_6$)alkyl optionally substituted by mono-, di-, or tri-halogen; (w) ($C_1$-$C_6$)alkoxy optionally substituted by mono-, di-, or tri-halogen; and (x) ($C_1$-$C_6$)alkylthio optionally substituted by mono-, di-, or tri-halogen;

each $R^7$ is independently (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di(($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl;

in each instance, independently, $R^{8a}$ and $R^{8b}$ are selected from (i) and (ii) as follows:
(i) $R^{8a}$ and $R^{8b}$ are each independently selected from (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di($C_1$-$C_6$)alkyl)carbamoyl, ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; and
(ii) each $R^{8a}$ and $R^{8b}$, together with the N to which they are bonded, independently form a 3 to 8 membered saturated or unsaturated ring optionally containing one or more O or S atoms, or one or more additional N atoms, in the ring;

each $R^9$ is independently hydrogen or ($C_1$-$C_6$)alkyl;

in each instance, independently, $R^{10}$ and $R^{11}$ are selected from (i) and (ii) as follows:
(i) $R^{10}$ and $R^{11}$ are each independently selected from (a) hydrogen; (b) ($C_1$-$C_6$)alkyl; (c) phenyl; (d) ($C_1$-$C_6$)alkyl substituted by aryl, hydroxy, carboxy, alkoxy, carbamoyl, ($C_1$-$C_6$)alkylcarbamoyl, di(($C_1$-$C_6$)alkyl)carbamoyl; ($C_3$-$C_7$)cycloalkylcarbamoyl or ($C_3$-$C_7$)heterocyclylcarbamoyl; (e) ($C_1$-$C_6$)alkyl substituted by mono-, di-, or tri-halogen; or (f) ($C_3$-$C_7$)cycloalkyl; and
(ii) each $R^{10}$ and $R^{11}$, together with the N to which they are bonded, independently form a 3 to 8 membered saturated or unsaturated ring optionally containing one or more O or S atoms, or one or more additional N atoms, in the ring;

in each instance, independently, $R^{12}$ and $R^{13}$ are selected from (i), (ii), (iii) and (iv) as follows:
(i) $R^{12}$ and $R^{13}$ are each independently selected from (a) hydrogen; (b) ($C_1$-$C_6$)alkyl; (c) phenyl; (d) ($C_1$-$C_6$)alkyl substituted by aryl, hydroxy, carboxy or alkoxy; (e) ($C_1$-$C_6$)alkyl substituted by mono-, di-, or tri-halogen; or (f) ($C_3$-$C_7$)cycloalkyl;
(ii) $R^{12}$ and $R^{13}$, together with the N to which they are bonded, form a 5 membered saturated ring containing at least one O or S atom, or at least one additional N atom, in the ring;
(iii) $R^{12}$ and $R^{13}$, together with the N to which they are bonded, form a 5 membered unsaturated ring, optionally containing one or more O or S atom, or one or more additional N atoms, in the ring; and
(iv) $R^{12}$ and $R^{13}$, together with the N to which they are bonded, form a 3, 4, 6, 7 or 8 membered saturated or unsaturated ring, optionally containing one or more O or S atoms, or one or more additional N atoms, in the ring;

k is 0, 1 or 2; and each p is independently 1, 2, 3, 4, 5 or 6.

8. The compound of claim 7, wherein $R^2$ is halogen.

9. The compound of claim 7, wherein $R^{4a}$ and $R^{4b}$ are each independently hydrogen.

10. The compound of claim 7, wherein
$R^6$ is aryl or heteroaryl, wherein said aryl and heteroaryl are optionally substituted with one or more substituents selected from the group consisting of (a) halogen; (b) cyano; (c) nitro; (d) hydroxy; (e) —$NR^{14}R^{15}$; (f) —C(O)$R^9$; (g) —C(O)$NR^{8a}R^{8b}$; (h) —$NR^7$C(O)$R^9$; (i) —OC(O)$NR^{8a}R^{8b}$; (j) —$NR^7$C(O)$OR^9$; (k) —C(O)$OR^9$; (l) guanidino; (m) heterocyclyl; (n) phenyl; (o) phenyloxy; (p) benzyl; (q) benzyloxy; (r) sulfamoyl; (s) ($C_1$-$C_6$)alkylsulfonyl; (t) ($C_1$-$C_6$)alkylaminosulfonyl; (u) di($C_1$-$C_6$)alkylaminosulfonyl; (v) ($C_1$-$C_6$)alkyl optionally substituted by mono-, di-, or tri-halogen; (w) ($C_1$-$C_6$)alkoxy optionally substituted by mono-, di-, or tri-halogen; and (x) ($C_1$-$C_6$)alkylthio optionally substituted by mono-, di-, or tri-halogen;

each $R^7$ is independently hydrogen or ($C_1$-$C_6$)alkyl;

in each instance, independently, $R^{8a}$ and $R^{8b}$ are selected from (i) or (ii) as follows:
(i) $R^{8a}$ and $R^{8b}$ are each independently selected from hydrogen or ($C_1$-$C_6$)alkyl; or
(ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

in each instance, independently, $R^{14}$ and $R^{15}$ are selected from (i) or (ii) as follows:
(i) $R^{14}$ and $R^{15}$ are each independently selected from (a) hydrogen; (b) ($C_1$-$C_6$)alkyl; (c) phenyl; (d) ($C_1$-$C_6$)alkyl substituted by aryl, hydroxy, carboxy or alkoxy; (e) ($C_1$-$C_6$)alkyl substituted by mono-, di-, or tri-halogen; or (f) ($C_3$-$C_7$)cycloalkyl; or
(ii) each $R^{14}$ and $R^{15}$, together with the N to which they are bonded, independently may form a 3 to 8 membered saturated or unsaturated ring optionally containing one or more O or S atoms, or one or more additional N atoms, in the ring.

11. The compound of claim 7, having formula III:

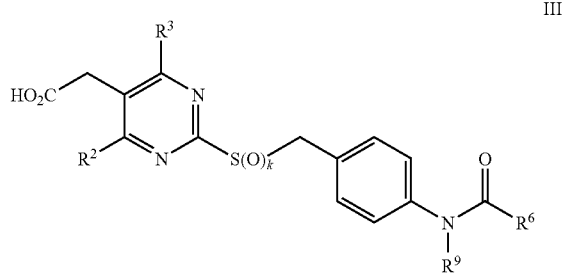

or a pharmaceutically acceptable salt, stereoisomer or tautomer thereof, wherein $R^9$ is hydrogen.

12. The compound of claim 11, wherein
$R^6$ is aryl or heteroaryl, wherein said aryl and heteroaryl are optionally substituted with one or more substituents selected from the group consisting of (a) halogen; (b) cyano; (c) nitro; (d) hydroxy; (e) —$NR^{14}R^{15}$; (f) —C(O)$R^9$; (g) —C(O)$NR^{8a}R^{8b}$; (h) —$NR^7$C(O)$R^9$; (i) —OC(O)$NR^{8a}R^{8b}$; (j) —$NR^7$C(O)$OR^9$; (k) —C(O)$OR^9$; (l) guanidino; (m) heterocyclyl; (n) phenyl; (o) phenyloxy; (p) benzyl; (q) benzyloxy; (r) sulfamoyl; (s) ($C_1$-$C_6$)alkylsulfonyl; (t) ($C_1$-$C_6$)alkylaminosulfonyl; (u) di($C_1$-$C_6$)alkylaminosulfonyl; (v) ($C_1$-$C_6$)alkyl optionally substituted by mono-, di-, or tri-halogen; (w) $(C_1-C_6)$ alkoxy optionally substituted by mono-, di-, or tri-halogen; and (x) $(C_1-C_6)$alkylthio optionally substituted by mono-, di-, or tri-halogen;

each $R^7$ is independently hydrogen or $(C_1-C_6)$alkyl;

in each instance, independently, $R^{8a}$ and $R^{8b}$ are selected from (i) or (ii) as follows:
  (i) $R^{8a}$ and $R^{8b}$ are each independently selected from hydrogen or $(C_1-C_6)$alkyl; or
  (ii) each $R^{8a}$ and $R^{8b}$, together with the N to which they are bonded, independently may form a 3 to 8 membered saturated or unsaturated ring optionally containing one or more O or S atoms, or one or more additional N atoms, in the ring;

in each instance, independently, $R^{14}$ and $R^{15}$ are selected from (i) or (ii) as follows:
  (i) $R^{14}$ and $R^{15}$ are each independently selected from (a) hydrogen; (b) $(C_1-C_6)$alkyl; (c) phenyl; (d) $(C_1-C_6)$ alkyl substituted by aryl, hydroxy, carboxy or alkoxy; (e) $(C_1-C_6)$alkyl substituted by mono-, di-, or tri-halogen; or (f) $(C_3-C_7)$cycloalkyl; or
  (ii) each $R^{14}$ and $R^{15}$, together with the N to which they are bonded, independently may form a 3 to 8 membered saturated or unsaturated ring optionally containing one or more O or S atoms, or one or more additional N atoms, in the ring.

13. The compound of claim 7 wherein $R^2$ and $R^3$ are each —N(CH$_3$)$_2$.

14. The compound of claim 7, having formula IV:

IV

[chemical structure]

or a pharmaceutically acceptable salt, stereoisomer or tautomer thereof, wherein
$R^2$ is halogen;
each $R^{16}$ is independently (a) hydrogen (b) halogen; (c) cyano; (d) nitro; (e) hydroxy; (f) —NR$^{8a}$R$^{8b}$; (g) —C(O)R$^9$; (h) —C(O)NR$^{8a}$R$^{8b}$; (i) —NR$^7$C(O)R$^9$; (j) —OC(O)NR$^{8a}$R$^{8b}$; (k) —NR$^7$C(O)OR$^9$; (l) —C(O)OR$^9$; (m) guanidino; (n) heterocyclyl; (o) phenyl; (p) phenyloxy; (q) benzyl; (r) benzyloxy; (s) sulfamoyl; (t) $(C_1-C_6)$alkylsulfonyl; (u) $(C_1-C_6)$alkylaminosulfonyl; (v) di$(C_1-C_6)$alkylaminosulfonyl; (w) $(C_1-C_6)$alkyl optionally substituted by mono-, di-, or tri-halogen; (x) $(C_1-C_6)$alkoxy optionally substituted by mono-, di-, or tri-halogen; and (y) $(C_1-C_6)$ alkylthio optionally substituted by mono-, di-, or tri-halogen; and
q is 0, 1, 2, 3, 4 or 5.

15. The compound of claim 14, wherein
each $R^{16}$ is independently (a) hydrogen (b) halogen; (c) cyano; (d) nitro; (e) hydroxy; (f) —NH$_2$; (g) —NH(C$_1$-C$_6$)alkyl; (h) —N((C$_1$-C$_6$)alkyl)$_2$; (i) —NHC(O)(C$_1$-C$_6$)alkyl; (j) —C(O)(C$_1$-C$_6$)alkyl; (k) —CO$_2$H; (l) —C(O)O(C$_1$-C$_6$)alkyl; (m) phenyl; (n) phenyloxy; (o) benzyl; (p) benzyloxy; (q) sulfamoyl; (r) $(C_1-C_6)$alkylsulfonyl; (s) $(C_1-C_6)$alkylaminosulfonyl; (t) di$(C_1-C_6)$ alkylaminosulfonyl; (u) $(C_1-C_6)$alkyl optionally substituted by mono-, di-, or tri-halogen; (v) $(C_1-C_6)$alkoxy optionally substituted by mono-, di-, or tri-halogen; or (w) $(C_1-C_6)$alkylthio optionally substituted by mono-, di-, or tri-halogen.

16. The compound of claim 7, having formula V:

V

[chemical structure]

or a pharmaceutically acceptable salt, stereoisomer or tautomer thereof.

17. The compound of claim 16 wherein $R^2$ is halogen.

18. The compound of claim 16 wherein
$R^2$ is halogen; and
$R^3$ is —N(CH$_3$)$_2$.

19. The compound of claim 16 wherein $R^2$ and $R^3$ are each independently —N(CH$_3$)$_2$.

20. The compound of claim 1, having the formula

[chemical structure]

or a pharmaceutically acceptable salt or tautomer thereof.

21. Th compound of claim 1, having the formula

[chemical structure]

or a pharmaceutically acceptable salt, solvate, hydrate or tautomer thereof.

22. The compound of claim 1, having the formula

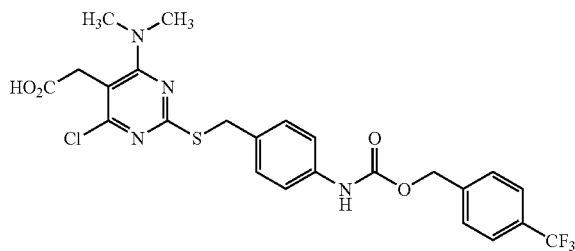

or a pharmaceutically acceptable salt or tautomer thereof.

23. The compound of claim 1, having the formula

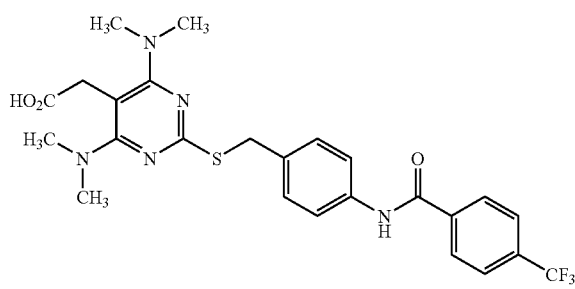

or a pharmaceutically acceptable salt or tautomer thereof.

24. The compound of claim 1, having the formula

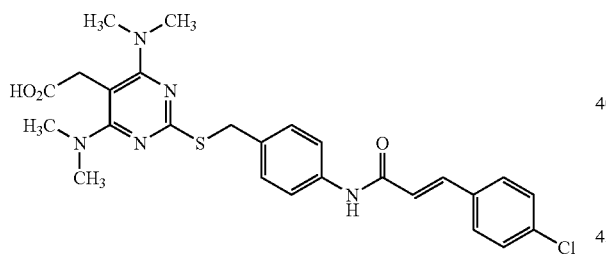

or a pharmaceutically acceptable salt, stereoisomer or tautomer thereof.

25. The compound of claim 1, having the formula

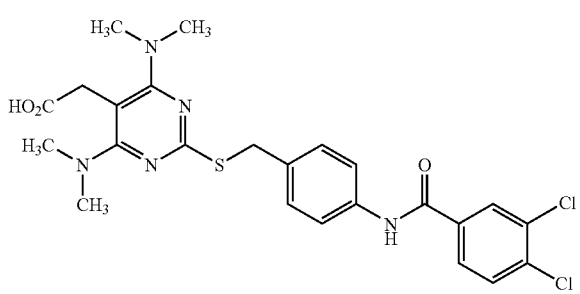

or a pharmaceutically acceptable salt or tautomer thereof.

26. The compound of claim 1, having the formula

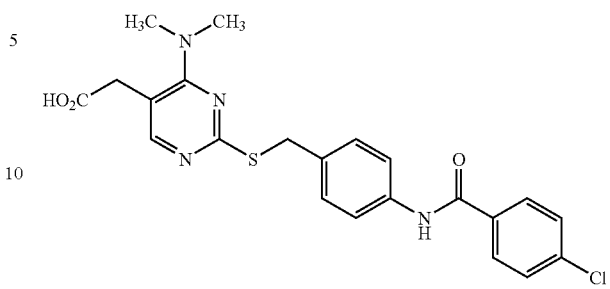

or a pharmaceutically acceptable salt or tautomer thereof.

27. The compound of claim 1, having the formula

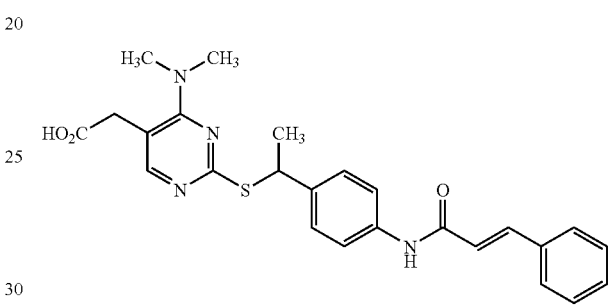

or a pharmaceutically acceptable salt, stereoisomer or tautomer thereof.

28. The compound of claim 1, having the formula

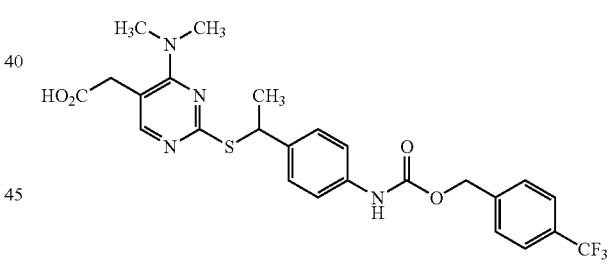

or a pharmaceutically acceptable salt, stereoisomer or tautomer thereof.

29. The compound of claim 1, having the formula

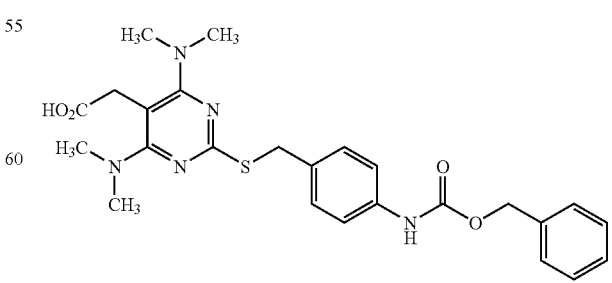

or a pharmaceutically acceptable salt, or tautomer thereof.

30. The compound of claim 1, having the formula

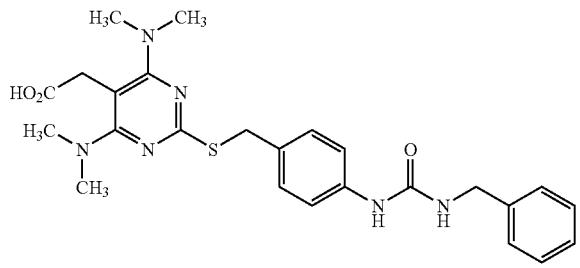

or a pharmaceutically acceptable salt, or tautomer thereof.

31. The compound of claim 1, having formula VI

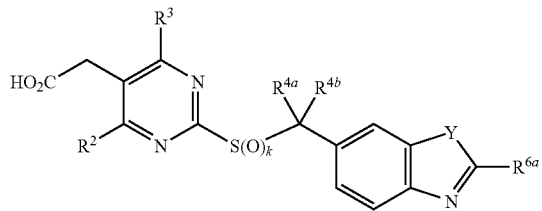

or a pharmaceutically acceptable salt, stereoisomer or tautomer thereof, wherein Y is NH, O or S; and $R^{6a}$ is (a) hydrogen; (b) halogen; (c) cyano; (d) nitro; (e) hydroxy; (f) phenyl; (g) phenyloxy; (h) benzyl; (i) benzyloxy; (j) guanidino; (k) heterocyclyl; (l) —$NR^{14}R^{15}$; (m) sulfamoyl; (n) ($C_1$-$C_6$)alkylsulfonyl; (O) ($C_1$-$C_6$)alkylaminosulfonyl; (p) di($C_1$-$C_6$)alkylaminosulfonyl; (q) —$C(O)R^9$; (r) —$C(O)OR^9$; (s) —$C(O)NR^{8a}R^{8b}$; (t) —$NR^7C(O)R^9$; (u) —$OC(O)NR^{8a}R^{8b}$; (v) —$NR^7C(O)OR^9$; (w) ($C_2$-$C_6$)alkenyl; (x) ($C_1$-$C_6$alkyl) optionally substituted by mono-, di-, or tri-halogen; (y) ($C_1$-$C_6$) alkoxy optionally substituted by mono-, di-, or tri-halogen; or (z) ($C_1$-$C_6$)alkylthio optionally substituted by mono-, di-, or tri-halogen.

32. A pharmaceutical composition comprising a compound of claim 1 and one or more pharmaceutically acceptable carriers or excipients.

33. A method for treating asthma or one or more symptoms thereof, the method comprising administering a compound of claim 1.

34. The method of claim 33, wherein the asthma is exercise induced asthma.

35. The method of claim 33, wherein the compound is administered orally, parenterally or topically.

36. The method of claim 33, wherein the compound is administered in combination with a second therapeutic agent.

37. The method of claim 36, wherein the second therapeutic agent is useful for treating asthma, exercise induced asthma, allergic rhinitis, atopic dermatitis, allergic conjunctivitis, Churg-Strauss syndrome, sinusitis, basophilic leukemia, chronic urticaria, basophilic leukocytosis, psoriasis, eczema, inflammatory bowel disease, ulcerative colitis, Crohn's disease, COPD (chronic obstructive pulmonary disorder), arthritis, or a symptom thereof.

* * * * *